United States Patent
Kaula et al.

(10) Patent No.: US 9,767,255 B2
(45) Date of Patent: Sep. 19, 2017

(54) PREDEFINED INPUT FOR CLINICIAN PROGRAMMER DATA ENTRY

(71) Applicant: Greatbatch Ltd., Clarence, NY (US)

(72) Inventors: Norbert Kaula, Arvada, CO (US);
Yohannes Iyassu, Denver, CO (US);
Seth Kaufman, Louisville, CO (US);
Paul Landers, Broomfield, CO (US)

(73) Assignee: NUVECTRA CORPORATION, Plano, TX (US)

( * ) Notice: Subject to any disclaimer, the term of this patent is extended or adjusted under 35 U.S.C. 154(b) by 132 days.

(21) Appl. No.: 14/010,942

(22) Filed: Aug. 27, 2013

(65) Prior Publication Data

US 2014/0067411 A1 Mar. 6, 2014

Related U.S. Application Data

(60) Provisional application No. 61/697,151, filed on Sep. 5, 2012.

(51) Int. Cl.
*G06F 19/00* (2011.01)
*A61N 1/18* (2006.01)

(52) U.S. Cl.
CPC ...... *G06F 19/3418* (2013.01); *G06F 19/3406* (2013.01); *G06F 19/3481* (2013.01)

(58) Field of Classification Search
CPC ............ A61N 1/36128; A61N 1/37247; A61N 1/36185; A61N 1/36146; G06Q 50/02
USPC .......................................................... 705/2
See application file for complete search history.

(56) References Cited

U.S. PATENT DOCUMENTS

| 4,432,360 A | 2/1984 | Mumford et al. |
| 5,286,202 A | 2/1994 | De Gyarfas et al. |
| 5,304,206 A | 4/1994 | Baker, Jr. et al. |
| 5,312,446 A | 5/1994 | Holschbach et al. |
| 5,370,672 A | 12/1994 | Fowler et al. |
| 5,383,914 A | 1/1995 | O'Phelan |
| 5,421,830 A | 6/1995 | Epstein et al. |

(Continued)

FOREIGN PATENT DOCUMENTS

| EP | 1192972 | 4/2002 |
| EP | 2277586 | 1/2011 |

(Continued)

OTHER PUBLICATIONS

Synalink Features, SynaMed Web Page, http://synamed.com/synalinkFeatures.html., Copyright 2010, 2 pgs.

(Continued)

*Primary Examiner* — Hiep V Nguyen
(74) *Attorney, Agent, or Firm* — Haynes and Boone, LLP; Eric Li

(57) ABSTRACT

The present disclosure involves a method of entering data in a portable electronic device. A request is received from a healthcare professional to perform data entry in an input field. The request is received via a touch-sensitive user interface of the portable electronic device. In response to the request, a plurality of predefined suggestions is displayed as candidates for the data entry. A selection of one of the plurality of predefined suggestions by the healthcare professional is then detected. Thereafter, the selected predefined suggestion is automatically entered as the data entry in the input field.

41 Claims, 11 Drawing Sheets

(56) References Cited

U.S. PATENT DOCUMENTS

| | | | |
|---|---|---|---|
| 5,561,446 A * | 10/1996 | Montlick | G06F 3/0488 345/173 |
| 5,628,776 A | 5/1997 | Paul et al. | |
| 5,713,937 A | 2/1998 | Nappholz et al. | |
| 5,722,999 A | 3/1998 | Snell | |
| 5,724,996 A | 3/1998 | Piunti | |
| 5,819,740 A | 10/1998 | Muhlenberg | |
| 5,879,374 A | 3/1999 | Powers et al. | |
| 5,905,500 A | 5/1999 | Kamen et al. | |
| 5,938,690 A | 8/1999 | Law et al. | |
| 6,016,447 A | 1/2000 | Juran et al. | |
| 6,016,448 A | 1/2000 | Busacker et al. | |
| 6,052,624 A | 4/2000 | Mann | |
| 6,083,156 A | 7/2000 | Lisiecki | |
| 6,148,233 A | 11/2000 | Owen et al. | |
| 6,154,675 A | 11/2000 | Juran et al. | |
| 6,216,036 B1 | 4/2001 | Jenkins et al. | |
| 6,246,414 B1 | 6/2001 | Kawasaki | |
| 6,249,705 B1 | 6/2001 | Snell | |
| 6,278,890 B1 | 8/2001 | Chassaing et al. | |
| 6,307,554 B1 | 10/2001 | Arai et al. | |
| 6,308,102 B1 | 10/2001 | Sieracki et al. | |
| 6,345,200 B1 | 2/2002 | Mouchawar et al. | |
| 6,386,882 B1 | 5/2002 | Linberg | |
| 6,442,432 B2 | 8/2002 | Lee | |
| 6,525,727 B1 | 2/2003 | Junkins et al. | |
| 6,564,104 B2 | 5/2003 | Nelson et al. | |
| 6,587,104 B1 | 7/2003 | Hoppe | |
| 6,611,267 B2 | 8/2003 | Migdal et al. | |
| 6,622,048 B1 | 9/2003 | Mann et al. | |
| 6,669,631 B2 | 12/2003 | Norris et al. | |
| 6,786,405 B2 | 9/2004 | Wiedenhoefer | |
| 6,852,080 B2 | 2/2005 | Bardy | |
| 6,882,982 B2 | 4/2005 | McMenimen et al. | |
| 6,895,280 B2 | 5/2005 | Meadows et al. | |
| 6,920,360 B2 | 7/2005 | Lee et al. | |
| 6,931,155 B1 | 8/2005 | Gioia | |
| 6,961,448 B2 | 11/2005 | Nichols et al. | |
| 6,961,617 B1 | 11/2005 | Snell | |
| 7,003,349 B1 | 2/2006 | Andersson et al. | |
| 7,034,823 B2 | 4/2006 | Dunnett | |
| 7,058,453 B2 | 6/2006 | Nelson et al. | |
| 7,060,030 B2 | 6/2006 | Von Arx et al. | |
| 7,065,409 B2 | 6/2006 | Mazar | |
| 7,066,910 B2 | 6/2006 | Bauhahn et al. | |
| 7,076,303 B2 | 7/2006 | Linberg | |
| 7,087,015 B1 | 8/2006 | Comrie et al. | |
| 7,092,761 B1 | 8/2006 | Cappa et al. | |
| 7,107,102 B2 | 9/2006 | Daignault et al. | |
| 7,142,923 B2 | 11/2006 | North et al. | |
| 7,181,286 B2 | 2/2007 | Sieracki et al. | |
| 7,181,505 B2 | 2/2007 | Haller et al. | |
| 7,184,837 B2 | 2/2007 | Goetz | |
| 7,239,926 B2 | 7/2007 | Goetz | |
| 7,266,412 B2 | 9/2007 | Stypulkowski | |
| 7,299,085 B2 | 11/2007 | Bergelson et al. | |
| 7,359,751 B1 | 4/2008 | Erickson et al. | |
| 7,373,204 B2 | 5/2008 | Gelfand et al. | |
| 7,440,806 B1 | 10/2008 | Whitehurst et al. | |
| 7,452,336 B2 | 11/2008 | Thompson | |
| 7,463,927 B1 | 12/2008 | Chaouat | |
| 7,474,223 B2 | 1/2009 | Nycz et al. | |
| 7,481,759 B2 | 1/2009 | Whitehurst et al. | |
| 7,489,970 B2 | 2/2009 | Lee et al. | |
| 7,496,403 B2 | 2/2009 | Cao et al. | |
| 7,499,048 B2 | 3/2009 | Sieracki et al. | |
| 7,505,815 B2 | 3/2009 | Lee et al. | |
| 7,551,960 B2 | 6/2009 | Forsberg et al. | |
| 7,602,384 B2 | 10/2009 | Rosenberg et al. | |
| 7,617,002 B2 | 11/2009 | Goetz | |
| 7,627,372 B2 | 12/2009 | Vaisnys et al. | |
| 7,640,059 B2 | 12/2009 | Forsberg et al. | |
| 7,657,317 B2 | 2/2010 | Thacker et al. | |
| 7,685,005 B2 | 3/2010 | Riff et al. | |
| 7,711,603 B2 | 5/2010 | Vanker et al. | |
| 7,720,549 B2 | 5/2010 | Schroeppel et al. | |
| 7,747,330 B2 | 6/2010 | Nolan et al. | |
| 7,774,067 B2 | 8/2010 | Keacher et al. | |
| 7,778,710 B2 | 8/2010 | Propato | |
| 7,801,596 B2 | 9/2010 | Fischell et al. | |
| 7,801,611 B2 | 9/2010 | Persen et al. | |
| 7,805,199 B2 | 9/2010 | KenKnight et al. | |
| 7,822,483 B2 | 10/2010 | Stone et al. | |
| 7,853,323 B2 | 12/2010 | Goetz | |
| 7,885,712 B2 | 2/2011 | Goetz et al. | |
| 7,890,180 B2 | 2/2011 | Quiles | |
| 7,928,995 B2 | 4/2011 | Daignault | |
| 7,934,508 B2 | 5/2011 | Behm | |
| 7,940,933 B2 | 5/2011 | Corndorf | |
| 7,953,492 B2 | 5/2011 | Corndorf | |
| 7,953,612 B1 | 5/2011 | Palmese et al. | |
| 7,957,808 B2 | 6/2011 | Dawant et al. | |
| 7,978,062 B2 | 7/2011 | LaLonde et al. | |
| 7,991,482 B2 | 8/2011 | Bradley | |
| 8,014,863 B2 | 9/2011 | Zhang et al. | |
| 8,021,298 B2 | 9/2011 | Barid et al. | |
| 8,027,726 B2 | 9/2011 | Ternes | |
| 8,046,241 B1 | 10/2011 | Dodson | |
| 8,060,216 B2 | 11/2011 | Greenberg et al. | |
| 8,068,915 B2 | 11/2011 | Lee et al. | |
| 8,068,918 B2 | 11/2011 | Vallapureddy et al. | |
| 8,078,440 B2 | 12/2011 | Otto et al. | |
| 8,082,162 B2 | 12/2011 | Flood | |
| 8,121,702 B2 | 2/2012 | King | |
| 8,135,566 B2 | 3/2012 | Marshall et al. | |
| 8,140,160 B2 | 3/2012 | Pless et al. | |
| 8,140,167 B2 | 3/2012 | Donders et al. | |
| 8,160,328 B2 | 4/2012 | Goetz et al. | |
| 8,160,704 B2 | 4/2012 | Freeberg | |
| 8,165,385 B2 | 4/2012 | Reeves et al. | |
| 8,187,015 B2 | 5/2012 | Boyd et al. | |
| 8,200,324 B2 | 6/2012 | Shen et al. | |
| 8,200,340 B2 | 6/2012 | Skelton et al. | |
| 8,219,206 B2 | 7/2012 | Skelton et al. | |
| 8,233,991 B2 | 7/2012 | Woods et al. | |
| 8,246,680 B2 | 8/2012 | Betz et al. | |
| 8,249,713 B2 | 8/2012 | Fang et al. | |
| 8,255,060 B2 | 8/2012 | Goetz et al. | |
| 8,323,218 B2 | 12/2012 | Davis et al. | |
| 8,326,433 B2 | 12/2012 | Blum et al. | |
| 8,340,775 B1 | 12/2012 | Cullen et al. | |
| 8,382,666 B1 | 2/2013 | Mao et al. | |
| 8,386,032 B2 | 2/2013 | Bachinski et al. | |
| 8,401,666 B2 | 3/2013 | Skelton et al. | |
| 8,428,727 B2 | 4/2013 | Bolea et al. | |
| 2001/0037220 A1 | 11/2001 | Merry et al. | |
| 2003/0076301 A1 | 4/2003 | Tsuk et al. | |
| 2003/0107572 A1 | 6/2003 | Smith et al. | |
| 2003/0139652 A1 | 7/2003 | Kang et al. | |
| 2003/0171911 A1 | 9/2003 | Fairweather | |
| 2003/0177031 A1 | 9/2003 | Malek | |
| 2004/0078215 A1 * | 4/2004 | Dahlin | G06F 19/322 705/2 |
| 2004/0088374 A1 | 5/2004 | Webb et al. | |
| 2004/0122477 A1 | 6/2004 | Whitehurst et al. | |
| 2004/0210273 A1 | 10/2004 | Wang | |
| 2005/0107831 A1 | 5/2005 | Hill et al. | |
| 2005/0149356 A1 | 7/2005 | Cyr et al. | |
| 2005/0168460 A1 | 8/2005 | Razdan et al. | |
| 2005/0277872 A1 | 12/2005 | Colby et al. | |
| 2006/0089888 A1 | 4/2006 | Roger | |
| 2006/0100832 A1 | 5/2006 | Bowman | |
| 2006/0241720 A1 | 10/2006 | Woods et al. | |
| 2006/0242159 A1 | 10/2006 | Bishop et al. | |
| 2006/0282168 A1 | 12/2006 | Sherman et al. | |
| 2007/0078497 A1 | 4/2007 | Vandanacker | |
| 2007/0093998 A1 | 4/2007 | El-Baroudi et al. | |
| 2007/0179349 A1 | 8/2007 | Hoyme et al. | |
| 2007/0203537 A1 | 8/2007 | Goetz et al. | |
| 2007/0203538 A1 | 8/2007 | Stone et al. | |
| 2007/0203543 A1 | 8/2007 | Stone et al. | |
| 2007/0203545 A1 * | 8/2007 | Stone et al. | 607/59 |
| 2007/0213790 A1 | 9/2007 | Nolan et al. | |
| 2008/0004675 A1 | 1/2008 | King et al. | |

(56) References Cited

U.S. PATENT DOCUMENTS

| | | |
|---|---|---|
| 2008/0033303 A1 | 2/2008 | Wariar et al. |
| 2008/0046036 A1 | 2/2008 | King et al. |
| 2008/0103546 A1* | 5/2008 | Patel ............... G06F 19/3481 607/45 |
| 2008/0140161 A1 | 6/2008 | Goetz et al. |
| 2008/0177362 A1 | 7/2008 | Phillips et al. |
| 2008/0218517 A1 | 9/2008 | Holmdahl |
| 2008/0262565 A1 | 10/2008 | Bentwich |
| 2009/0018617 A1 | 1/2009 | Skelton et al. |
| 2009/0018619 A1 | 1/2009 | Skelton et al. |
| 2009/0024178 A1 | 1/2009 | Hennig |
| 2009/0048871 A1 | 2/2009 | Skomra |
| 2009/0089034 A1 | 4/2009 | Penney et al. |
| 2009/0099624 A1 | 4/2009 | Kokones et al. |
| 2009/0132009 A1 | 5/2009 | Torgenson et al. |
| 2009/0136094 A1 | 5/2009 | Driver et al. |
| 2009/0196471 A1 | 8/2009 | Goetz et al. |
| 2009/0234873 A1 | 9/2009 | Li et al. |
| 2009/0264967 A1 | 10/2009 | Giftakis et al. |
| 2009/0281596 A1 | 11/2009 | King et al. |
| 2010/0004033 A1 | 1/2010 | Choe et al. |
| 2010/0010566 A1 | 1/2010 | Thacker et al. |
| 2010/0010574 A1 | 1/2010 | Skelton et al. |
| 2010/0010580 A1 | 1/2010 | Skelton et al. |
| 2010/0058462 A1 | 3/2010 | Chow |
| 2010/0076534 A1 | 3/2010 | Mock |
| 2010/0090004 A1 | 4/2010 | Sands et al. |
| 2010/0106475 A1 | 4/2010 | Smith et al. |
| 2010/0123547 A1 | 5/2010 | Stevenson et al. |
| 2010/0152534 A1 | 6/2010 | Kim et al. |
| 2010/0161345 A1 | 6/2010 | Cain et al. |
| 2010/0198103 A1 | 8/2010 | Meadows et al. |
| 2010/0198304 A1 | 8/2010 | Wang |
| 2010/0222845 A1 | 9/2010 | Goetz |
| 2010/0223020 A1 | 9/2010 | Goetz |
| 2010/0265072 A1 | 10/2010 | Goetz et al. |
| 2010/0268304 A1 | 10/2010 | Matos |
| 2010/0280578 A1 | 11/2010 | Skelton et al. |
| 2011/0004059 A1 | 1/2011 | Arneson et al. |
| 2011/0015514 A1 | 1/2011 | Skalli et al. |
| 2011/0015693 A1 | 1/2011 | Williamson |
| 2011/0023343 A1 | 2/2011 | Turner et al. |
| 2011/0038498 A1 | 2/2011 | Edgar |
| 2011/0040546 A1 | 2/2011 | Gerber et al. |
| 2011/0040547 A1 | 2/2011 | Gerber et al. |
| 2011/0046697 A1 | 2/2011 | Gerber et al. |
| 2011/0054560 A1 | 3/2011 | Rosenberg et al. |
| 2011/0054870 A1 | 3/2011 | Dariush et al. |
| 2011/0077459 A1 | 3/2011 | Rofougaran |
| 2011/0077616 A1 | 3/2011 | Bennett et al. |
| 2011/0093030 A1 | 4/2011 | Goetz et al. |
| 2011/0093047 A1 | 4/2011 | Davis et al. |
| 2011/0093051 A1 | 4/2011 | Davis et al. |
| 2011/0153341 A1 | 6/2011 | Diaz-Cortes |
| 2011/0170739 A1 | 7/2011 | Gillam et al. |
| 2011/0172564 A1 | 7/2011 | Drew |
| 2011/0172737 A1 | 7/2011 | Davis et al. |
| 2011/0172744 A1 | 7/2011 | Davis et al. |
| 2011/0185178 A1 | 7/2011 | Gotthardt |
| 2011/0191275 A1 | 8/2011 | Lujan et al. |
| 2011/0224523 A1 | 9/2011 | Budiman |
| 2011/0246219 A1 | 10/2011 | Smith et al. |
| 2011/0264165 A1 | 10/2011 | Molnar et al. |
| 2011/0270358 A1 | 11/2011 | Davis et al. |
| 2011/0282414 A1 | 11/2011 | Kothandaraman et al. |
| 2011/0305376 A1 | 12/2011 | Neff |
| 2011/0307284 A1 | 12/2011 | Thompson et al. |
| 2011/0313268 A1 | 12/2011 | Kokones et al. |
| 2011/0313487 A1 | 12/2011 | Kokones et al. |
| 2012/0041518 A1 | 2/2012 | Kim et al. |
| 2012/0046715 A1 | 2/2012 | Moffitt et al. |
| 2012/0071947 A1 | 3/2012 | Gupta et al. |
| 2012/0083857 A1 | 4/2012 | Bradley et al. |
| 2012/0084689 A1 | 4/2012 | Ledet et al. |
| 2012/0089008 A1 | 4/2012 | Strehl et al. |
| 2012/0109230 A1 | 5/2012 | Kothandaraman et al. |
| 2012/0192874 A1 | 8/2012 | Bolea et al. |
| 2012/0239116 A1 | 9/2012 | Lee et al. |
| 2012/0256857 A1 | 10/2012 | Mak |
| 2012/0265269 A1 | 10/2012 | Lui et al. |
| 2012/0277828 A1 | 11/2012 | O'Conner et al. |
| 2012/0290041 A1 | 11/2012 | Kim et al. |
| 2012/0290272 A1 | 11/2012 | Bryan |
| 2012/0290976 A1 | 11/2012 | Lahm et al. |
| 2012/0296392 A1 | 11/2012 | Lee et al. |
| 2012/0296396 A1 | 11/2012 | Moffitt et al. |
| 2012/0296397 A1 | 11/2012 | Vansickle |
| 2012/0303087 A1 | 11/2012 | Moffitt et al. |
| 2012/0310300 A1 | 12/2012 | Kaula et al. |
| 2013/0023950 A1 | 1/2013 | Gauthier |
| 2013/0060299 A1 | 3/2013 | Polefko et al. |
| 2013/0060300 A1 | 3/2013 | Polefko et al. |
| 2013/0060301 A1 | 3/2013 | Polefko et al. |
| 2013/0060302 A1 | 3/2013 | Polefko et al. |
| 2013/0079848 A1 | 3/2013 | Campbell et al. |

FOREIGN PATENT DOCUMENTS

| | | |
|---|---|---|
| WO | WO 9959106 | 11/1999 |
| WO | WO 0209808 | 2/2002 |
| WO | WO 02084637 | 10/2002 |
| WO | WO 2009113102 | 9/2009 |
| WO | WO 2011028261 | 3/2011 |
| WO | WO 2011063248 | 5/2011 |
| WO | WO 2011104028 | 9/2011 |
| WO | WO 2011123669 | 10/2011 |
| WO | WO 2012018851 | 2/2012 |
| WO | WO 2012021862 | 2/2012 |
| WO | WO 2012135949 | 10/2012 |
| WO | WO 2013023085 | 2/2013 |

OTHER PUBLICATIONS

Boston Scientific Corporation, "Boston Scientific Precision Spectra System Programming Manual", Copyright 2010, 580 pgs.

* cited by examiner

PREDEFINED INPUT FOR CLINICIAN PROGRAMMER DATA ENTRY

PRIORITY DATA

The present application is a utility application of provisional U.S. Patent Application No. 61/697,151, filed on Sep. 5, 2012, entitled "Predefined Input for Clinician Programmer Data Entry," the disclosures of each of which are hereby incorporated by reference in their entirety.

BACKGROUND

As medical device technologies continue to evolve, active implanted medical devices have gained increasing popularity in the medical field. For example, one type of implanted medical device includes neurostimulator devices, which are battery-powered or battery-less devices that are designed to deliver electrical stimulation to a patient. Through proper electrical stimulation, the neurostimulator devices can provide pain relief for patients or restore bodily functions.

Implanted medical devices (for example a neurostimulator) can be controlled using an electronic programming device such as a clinician programmer or a patient programmer. These programmers can be used by medical personnel or the patient to define the particular electrical stimulation therapy to be delivered to a target area of the patient's body, alter one or more parameters of the electrical stimulation therapy, or otherwise conduct communications with a patient. However, data entry on existing programmers has been slow and inefficient. Users typically have to enter data manually by typing in each character one by one, either through a virtual keyboard or a physical one. This slow and inefficient data entry process is not only frustrating for the user, but it also greatly increases the likelihood of errors occurring during the data entry process.

Therefore, although existing neurostimulation devices and methods have been generally adequate for their intended purposes, they have not been entirely satisfactory in every aspect.

SUMMARY

One aspect of the present disclosure involves a portable electronic device configured to program stimulation parameters of an electrical stimulation therapy for a patient. The portable electronic device includes: a touch-sensitive user interface configured to receive an input from a user and display an output to the user; a memory storage configured to store programming instructions; one or more electronic processors configured to execute the programming instructions to perform the following steps: receiving, via the touch-sensitive user interface, a request from a healthcare professional to perform data entry in an input field; displaying, via the touch-sensitive user interface and in response to the receiving the request, a plurality of predefined suggestions as candidates for the data entry, wherein the predefined suggestions are customized for one of: the healthcare professional or the patient; detecting, via the touch-sensitive user interface, a selection of one of the plurality of predefined suggestions by the healthcare professional; and automatically entering the selected predefined suggestion as the data entry in the input field.

Another aspect of the present disclosure involves a medical system. The medical system includes: one or more medical devices configurable to deliver a medical therapy to a patient; and a portable electronic device having a touch-sensitive user interface through which data entry is performed with respect to the medical therapy, wherein the portable electronic device includes a non-transitory computer readable medium comprising executable instructions that when executed by a processor, causes the processor to perform the steps of: receiving, via the touch-sensitive user interface, a request from a healthcare professional to perform data entry in an input field; displaying, via the touch-sensitive user interface and in response to the receiving the request, a plurality of predefined suggestions as candidates for the data entry, wherein the predefined suggestions are customized for one of: the healthcare professional or the patient; detecting, via the touch-sensitive user interface, a selection of one of the plurality of predefined suggestions by the healthcare professional; and automatically entering the selected predefined suggestion as the data entry in the input field.

Yet another aspect of the present disclosure involves a method of entering data in a portable electronic device. The method includes: receiving, via a touch-sensitive user interface of the portable electronic device, a request from a healthcare professional to perform data entry in an input field; displaying, via the touch-sensitive user interface and in response to the receiving the request, a plurality of predefined suggestions as candidates for the data entry, wherein the predefined suggestions are customized for one of: the healthcare professional or the patient; detecting, via the touch-sensitive user interface, a selection of one of the plurality of predefined suggestions by the healthcare professional; and automatically entering the selected predefined suggestion as the data entry in the input field.

One more aspect of the present disclosure involves an apparatus for inputting data in a clinician programmer. The apparatus includes: means for receiving a request from a healthcare professional to perform data entry directed to a patient file in an input field; means for displaying a plurality of predefined suggestions as candidates for the data entry, wherein the predefined suggestions are customized for one of: the healthcare professional or the patient, and wherein the displaying comprises: assigning a respective rank to each of the plurality of predefined suggestions according to one or more predetermined criteria, and displaying the plurality of predefined suggestions according to their respective ranks, wherein the predetermined criteria include at least one of: frequency of past use of each of the predefined suggestions, and correlation between each of the predefined suggestions and an existing data content in the patient file; means for detecting a selection of one of the plurality of predefined suggestions by the healthcare professional; and means for automatically entering the selected predefined suggestion as the data entry in the input field.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

The use of active implanted medical devices has become increasingly prevalent over time. Some of these implanted medical devices include neurostimulator (also referred to as a pulse generator) devices that are capable of providing pain relief by delivering electrical stimulation to a patient. In that regards, electronic programmers have been used to configure or program these neurostimulators (or other types of suitable active implanted medical devices) so that they can be operated in a certain manner. These electronic programmers include clinician programmers and patient programmers, each of which may be a handheld device. For example, a clinician programmer allows a medical professional (e.g., a doctor or a nurse) to define the particular electrical stimulation therapy to be delivered to a target area of the patient's body, while a patient programmer allows a patient to alter one or more parameters of the electrical stimulation therapy.

In recent years, these electronic programmers have achieved significant improvements, for example, improvements in size, power consumption, lifetime, and ease of use. However, in spite of the numerous improvements in various areas, existing electronic programmers still have significant shortcomings with respect to data entry. For many existing programmers, data entry consists of a user manually typing in characters via a virtual keyboard of the electronic programmer. As such, existing electronic programmers suffer from the following drawbacks:

Healthcare professionals waste time typing out information character by character.

Common neural stimulation words and phrases must be re-entered every time they are used.

Paragraphs for standard procedural records, common symptoms, etc. must be re-entered frequently.

Errors in data entry are increased, a factor that slows down or prevents searchability and potentially creates misleading electronic medical records of patients.

If a stylus is missing, information input is impossible.

To address these drawbacks discussed above, the present disclosure offers a method and system of implementing predefined inputs for programmer data entry, as discussed below in more detail.

Figure 1:
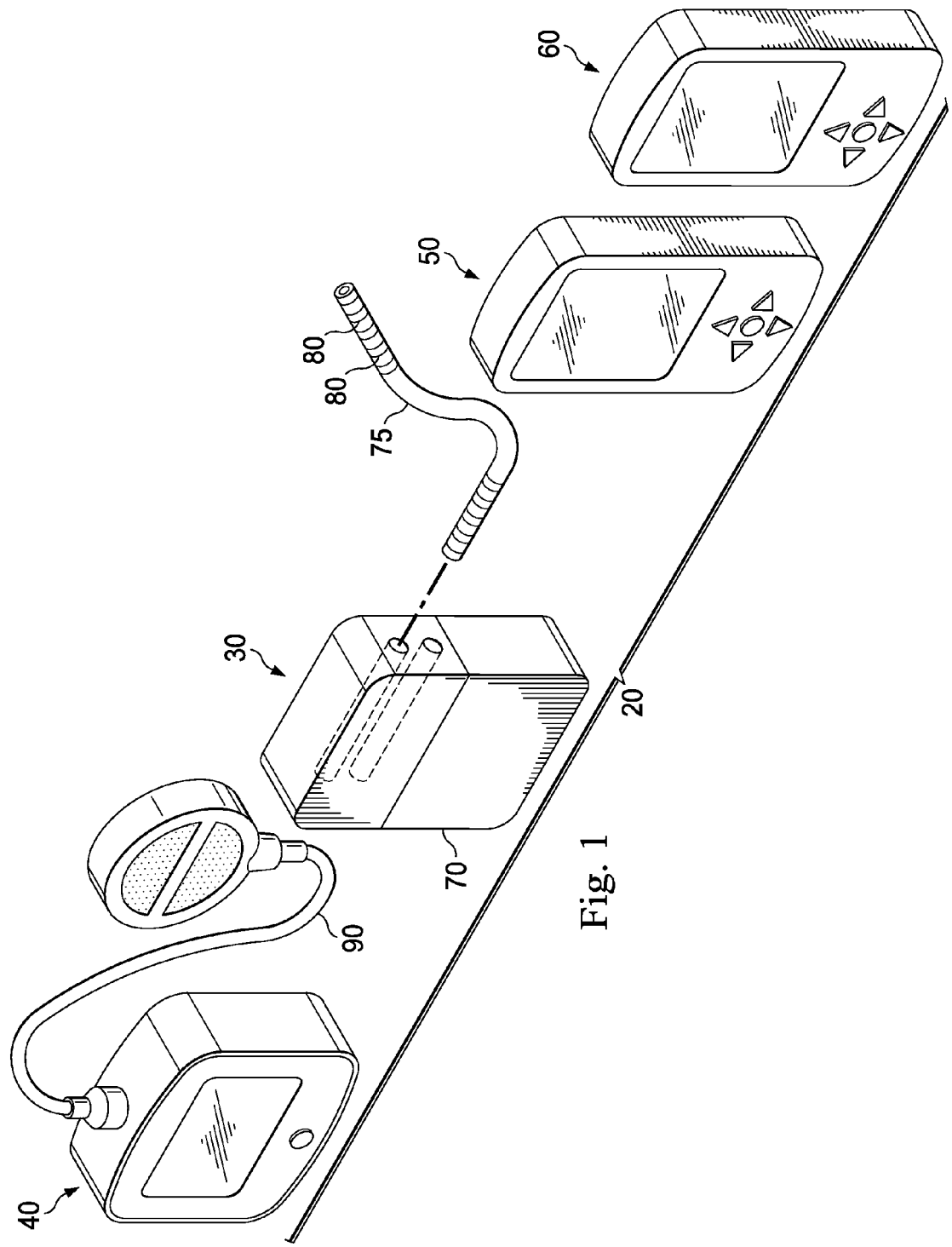
FIG. 1 is a simplified block diagram of an example medical system according to various aspects of the present disclosure.

FIG. 1 is a simplified block diagram of a medical device system 20 is illustrated to provide an example context of the various aspects of the present disclosure. The medical system 20 includes an implantable medical device 30, an external charger 40, a patient programmer 50, and a clinician programmer 60. The implantable medical device 30 can be implanted in a patient's body tissue. In the illustrated embodiment, the implantable medical device 30 includes an implanted pulse generator (IPG) 70 that is coupled to one end of an implanted lead 75. The other end of the implanted lead 75 includes multiple electrode surfaces 80 through which electrical current is applied to a desired part of a body tissue of a patient. The implanted lead 75 incorporates electrical conductors to provide a path for that current to travel to the body tissue from the IPG 70. Although only one implanted lead 75 is shown in FIG. 1, it is understood that a plurality of implanted leads may be attached to the IPG 70.

Although an IPG is used here as an example, it is understood that the various aspects of the present disclosure apply to an external pulse generator (EPG) as well. An EPG is intended to be worn externally to the patient's body. The EPG connects to one end (referred to as a connection end) of one or more percutaneous, or skin-penetrating, leads. The other end (referred to as a stimulating end) of the percutaneous lead is implanted within the body and incorporates multiple electrode surfaces analogous in function and use to those of an implanted lead.

The external charger 40 of the medical device system 20 provides electrical power to the IPG 70. The electrical power may be delivered through a charging coil 90. In some embodiments, the charging coil can also be an internal component of the external charger 40. The IPG 70 may also incorporate power-storage components such as a battery or capacitor so that it may be powered independently of the external charger 40 for a period of time, for example from a day to a month, depending on the power requirements of the therapeutic electrical stimulation delivered by the IPG.

The patient programmer 50 and the clinician programmer 60 may be portable handheld devices that can be used to configure the IPG 70 so that the IPG 70 can operate in a certain way. The patient programmer 50 is used by the patient in whom the IPG 70 is implanted. The patient may adjust the parameters of the stimulation, such as by selecting a program, changing its amplitude, frequency, and other parameters, and by turning stimulation on and off. The clinician programmer 60 is used by a medical personnel to configure the other system components and to adjust stimulation parameters that the patient is not permitted to control, such as by setting up stimulation programs among which the patient may choose, selecting the active set of electrode surfaces in a given program, and by setting upper and lower limits for the patient's adjustments of amplitude, frequency, and other parameters.

In the embodiments discussed below, the clinician programmer 60 is used as an example of the electronic programmer. However, it is understood that the electronic programmer may also be the patient programmer 50 or other touch screen programming devices (such as smart-phones or tablet computers) in other embodiments.

Figure 2:
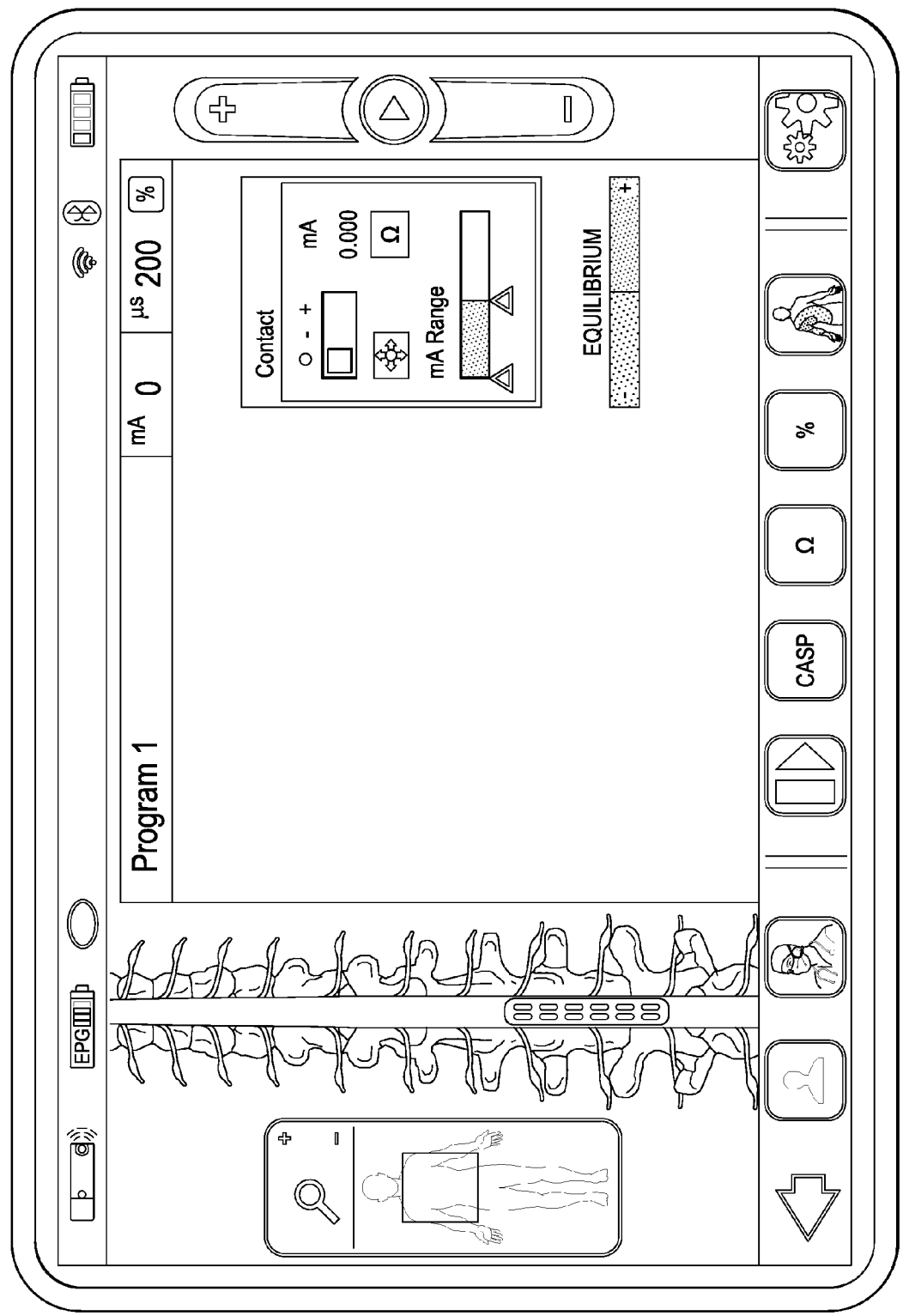
FIGS. 2-4 illustrate an embodiment of a user interface for performing data entry according to various aspects of the present disclosure.
Figure 3:
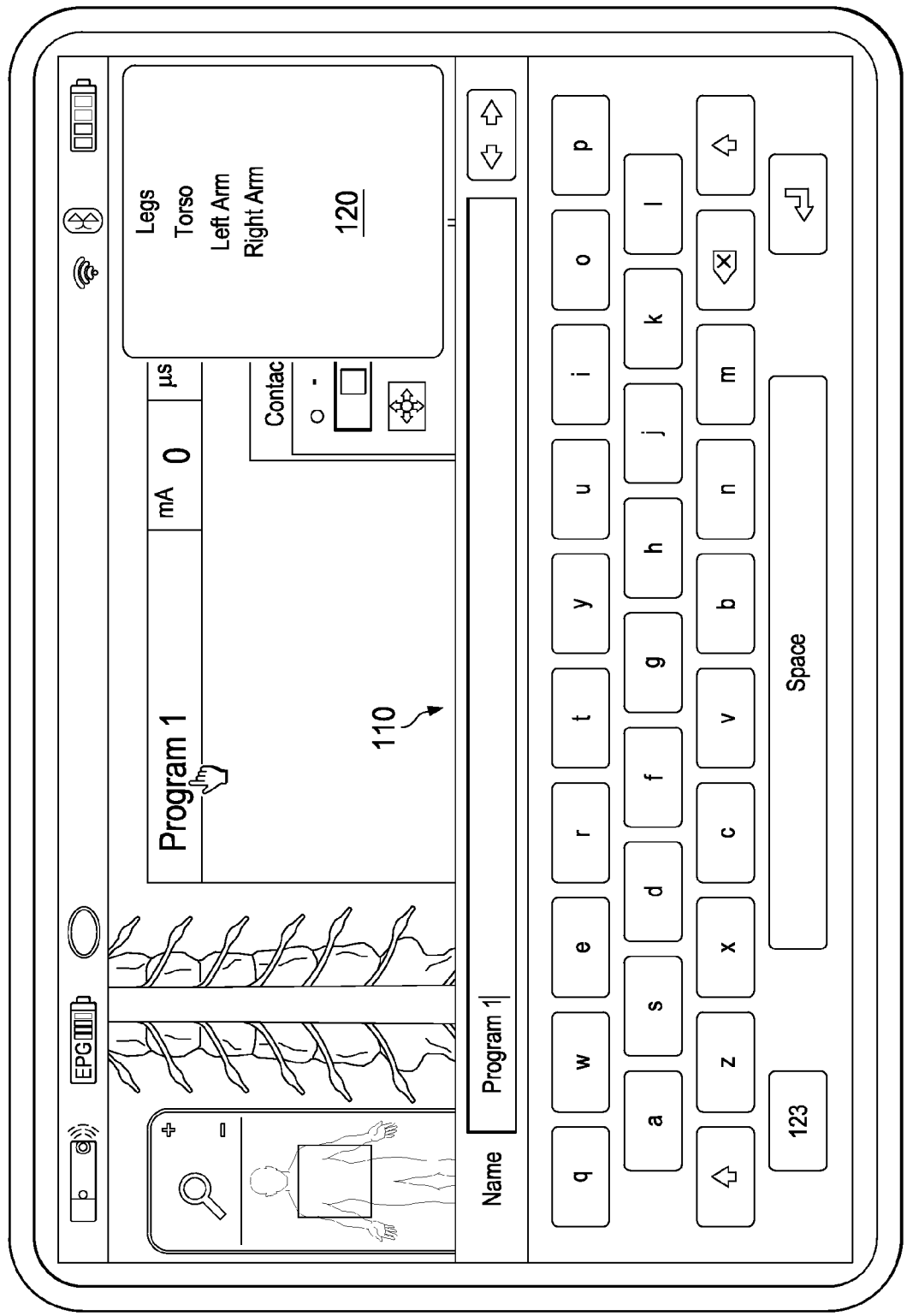
Figure 4:
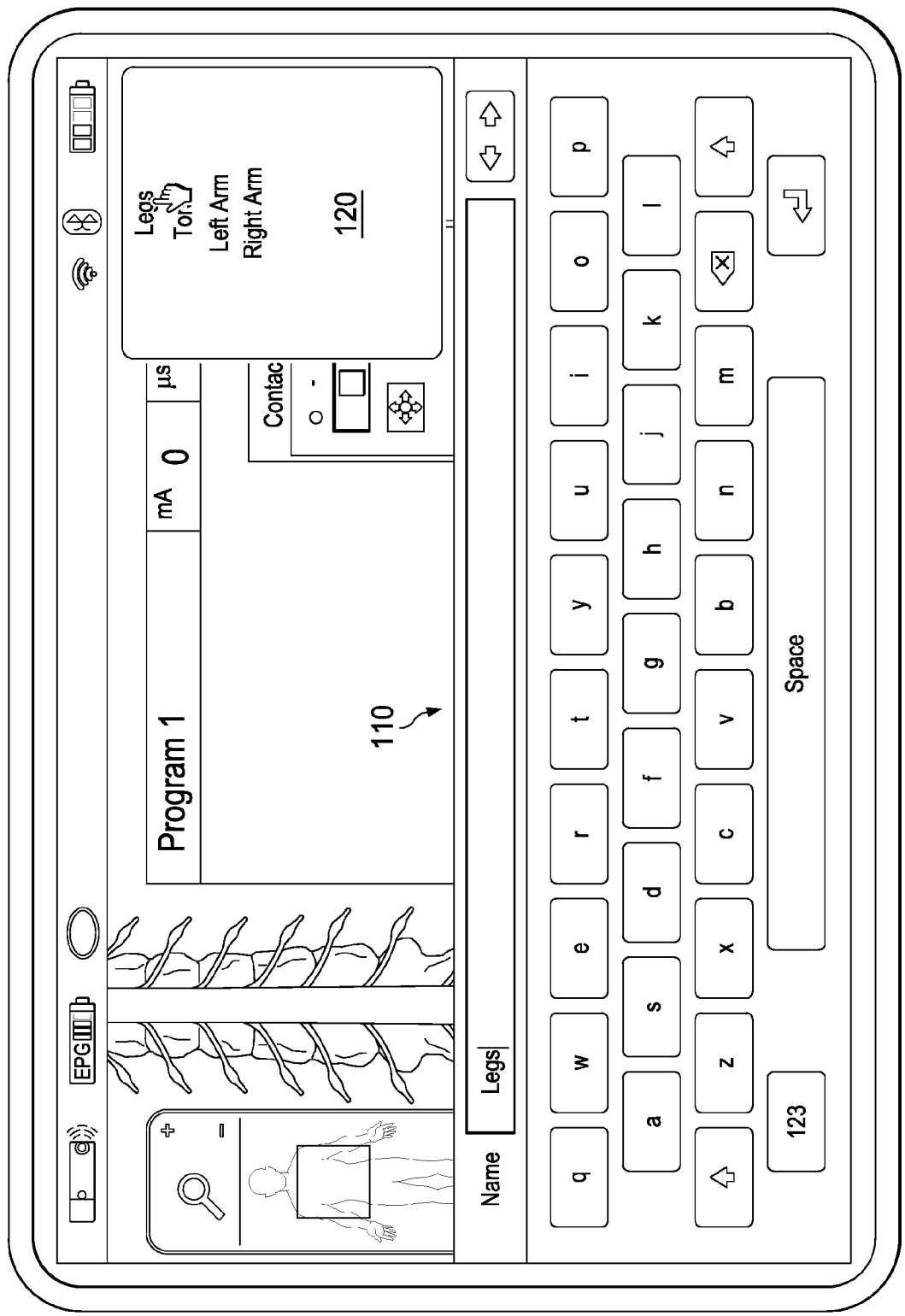

FIGS. 2-4 illustrate an embodiment of a user interface 100 implemented on an example clinician programmer 60. Specifically, the portions of the user interface 100 shown in FIGS. 2-4 illustrate the presentation of predefined data entries (or preset responses) according to the various aspects of the present disclosure. In some embodiments, the user interface 100 may be displayed on a screen of a programmer, for example a capacitive or resistive touch-sensitive display. In other embodiments, the user interface 100 may be displayed on a programmer and an external monitor simultaneously, for example in accordance with U.S. patent application Ser. No. 13/600,875, filed on Aug. 31, 2012, entitled "Clinician Programming System and Method", the disclosure of which is hereby incorporated by reference in its entirety. As such, both the healthcare provider (e.g., the target user of the user interface 100) and the patient are able to view the user interface 100 at the same time.

Referring to FIG. 2, the user interface 100 allows a user (e.g., a healthcare professional) to perform data entry for a patient file. The patient file may include a variety of information related to the patient and/or the treatment for the patient, such as the patient's name, address, occupation, gender, ethnicity, past medical history, current treatment plans, etc. In the example shown in FIG. 2, the user interface 100 illustrates an example programming screen for programming stimulation parameters for an electrical stimulation therapy to be delivered to a patient, for example by the IPG 70 of FIG. 1. As examples, these stimulation parameters may include stimulation current, pulse width, frequency, and electrode polarity or configuration. A programmed group of stimulation parameters and/or other programmable details collectively corresponds to a "stimulation program." In the user interface 100 shown in FIG. 2, the stimulation program has a default name of "Program 1." However, this default name for the stimulation program may not be sufficiently descriptive. As such, the user (e.g., a healthcare professional) may wish to change the name "Program 1" to another more descriptive name. As discussed above, existing electronic programmers typically require the user to manually type in a new program name character by character, which is inefficient and error-prone.

According to the various aspects of the present disclosure, the user interface 100 of the clinician programmer 60 allows suitable or appropriate program names to be automatically suggested. Referring to FIG. 3, when the user clicks on the program name "Program 1", a text input field 110 appears. The input field 110 is accompanied by a virtual keyboard in the illustrated embodiment, but it is understood that other suitable input devices may be used in other embodiments, such as a physical keyboard. The user may edit the program name (for example by using the virtual keyboard) in the input field 110.

To facilitate the editing of the program name, the user interface 100 also displays a list of suggested program names 120. In the illustrated embodiment, the suggested program names 120 are displayed as a drop-down list adjacent to the input field 110. In other embodiments, the suggested program names 120 may be displayed as a list of suggestions floating above the specific data entry field. As examples shown in FIG. 4, the list of suggested program names 120 include "Legs", "Torso", "Left Arm", and "Right Arm."

Referring to FIG. 4, the user may click on "Legs" in the suggested list of program names 120. As a result, the name of the program is automatically changed into "Legs" in the input field 110. The user may now further edit the name "Legs" if he wishes to do so. Similarly, the user may click on any of the other names in the suggested list of program names 120 to automatically change the data entry in the input field 110 to the new selected program name. As such, the speed and efficiency in which the user performs data entry is greatly increased. The user is no longer required to manually type in a desired entry character by character. Instead, the user may choose from a plurality of predefined data entries (e.g., the program names 120) to perform data entry quickly.

The suggested list of program names 120 are a form of preset responses or predefined data entries according to the present disclosure. These predefined data entries are applicable to a variety of information inputs. In one embodiment, the data entries can be suggested based on the first few characters typed by the user. For example, suppose an attending physician's name is John Doe. As the user is entering the attending physician's name, for example by typing "Jo" or "D", a list of physician's names would appear. The name that best matches the characters input by the user appears at the beginning of the list.

In some other embodiments, common or popular data entries for each input field are preloaded on the clinician programmer. These common or popular data entries may be presented whether or not the user inputs any data. In some embodiments, these common or popular data entries are defined by a healthcare professional, for example the user of the clinician programmer. The healthcare professional may define a list of popular phrases, words, sentences, names, etc., that he/she knows will be frequently used. These phrases, words, names, sentences or other suitable types of data entry need not be related to just the names of the stimulation program. They may pertain to any other part of the patient file, such as the patient's personal or biographical information, past medical history, or past surgical procedures performed on the patient. In other words, the healthcare professional can generate his/her own database of popular data entries. Since the database is defined by the healthcare professional, it is customized to the healthcare professional. For example, the popular data entries defined by healthcare professional A (and residing in the database generated by that healthcare professional A) may not necessarily be useful or suitable for the popular data entries for healthcare professional B, who may have generated his/her own database of popular data entries based on his/her preferences. The customized database for popular data entries may be stored on the clinician programmer locally, or stored in a remote server. In any case, as a given healthcare professional is using the clinician programmer to perform data entry, the suggested candidates for data entries (e.g., the program names 120) would be selected from the data entries stored in the customized database.

Alternatively, the common or popular data entries may also be generated by analyzing popular data entries that are stored on other clinician programmers, or popular data entries that are stored on a remote electronic server. These data entries reflect what other healthcare professionals consider to be popular or frequently used terms, phrases, sentences, or words, etc. Thus, a user herein may import these popular data entries (or just a subset thereof) into the popular data entry database on his/her own clinician programmer. Of course, the user may customize his/her database of popular data entries by defining some of the popular data entries, and importing other popular data entries from external devices.

In some embodiments, the popular data entries may include a relatively long entry such as a paragraph describing details of a medical procedure, common symptoms of an illness, or side effects of a medicine. In these cases, the paragraphs can be presented with blank spaces reserved for patient specifics (e.g., the patient's name, address, or other patient-specific biographical or medical information). For example, such paragraph may include a phrase "An implant of a percutaneous lead in the lumbar region for lower back pain", or another suitable frequently-used phrase.

In some embodiments, the predefined data entries may be generated based on the content of existing data in the patient file. For example, the existing data in a patient file may frequently mention knee pain or treatment for ailing knees. The clinician programmer of the present disclosure may analyze the existing data in the patient file, for example by searching for frequently-used keywords such as "pain" or parts of the human body. As a result of this analysis, the clinician programmer of the present disclosure detects that knee pain is a prominent issue for this specific patient for which data entry is performed. Consequently, the clinician programmer may recommend a list of predefined data entries that are related to knee pain in some manner.

According to the various aspects of the present disclosure, the clinician programmer can also present the suggested predefined data entries in a ranked manner. The ranking of each predefined data entry may be assigned by the clinician programmer before these data entries are presented. In some embodiments, the ranking is done as a function of the data entry's relevancy to keywords in the patient's file. For example, in the knee pain example discussed above, since the existing data in the patient file frequently mentions knee pain, then when the healthcare professional starts to input symptoms in the symptoms field, common symptoms and consequences of knee pain will be listed at the beginning of the suggestions. In other words, the data entries that are most relevant to the knee pain are ranked higher than other data entries and presented ahead of other data entries.

In some other embodiments, the ranking may also be done as a function of each date entry's previous usage or frequency of usage. For example, if the program name "Leg" has been the most frequently-used program name for a particular clinician programmer based on past history, then the name "Leg" is assigned the highest ranking among all program names and will be presented first to the user when the program names 120 are shown to the user.

In yet other embodiments, the ranking may be done as a function of a proximity of an external device's proximity to the clinician programmer. For example, when the healthcare professional starts entering data about a patient's medical device or about a patient with a medical device, the clinician programmer locates medical devices with wireless communication capabilities and within communication range to the clinician programmer. The clinician programmer then ranks those devices above other devices not in close proximity. And among these medical devices within communication range, the devices that are closer to the clinician programmer are also ranked higher than the devices that are farther away.

Figure 5:
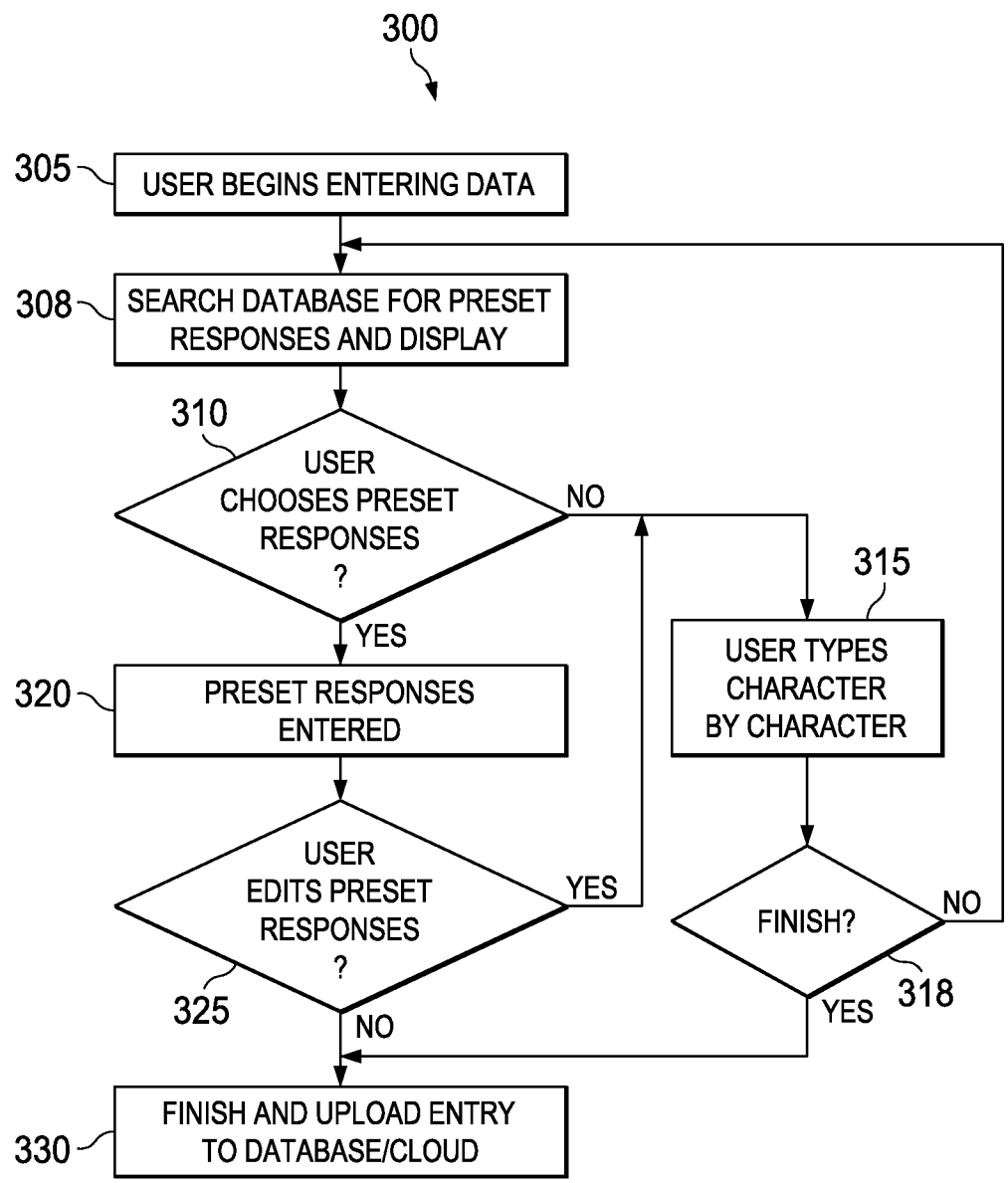
FIGS. 5, 6A-6B, and 7 are simplified flowcharts illustrating methods of performing data entry on an electronic programmer according to various aspects of the present disclosure.

FIG. 5 is a simplified flowchart of a method 300 of input data into a clinician programmer according to the various aspects of the present disclosure. The method 300 includes a step 305, in which the user of a clinician programmer begins entering data into the clinician programmer through a user interface of the clinician programmer. The method 300 includes a step 308, in which a database is searched for preset responses. These preset responses are then displayed. The method 300 then proceeds to a decision step 310 to determine if the user has chosen one of the preset responses. If the answer from the decision step 310 is no, then the method 300 continues to a step 315, in which the user types the data entry character by character. In some alternative embodiments, the data entry need not be done by the user character by character. Instead, the clinician programmer may be communicatively coupled to a network, for example a cloud-computing network, through which the data entry may incorporate an autocomplete feature. The method then proceeds to a decision step 318 to determine if the data entry is finished. If the answer from the decision step 318 is no, then the method 300 loops back to step 308 again. If the answer from the decision step 318 is yes, then the method concludes at step 330, in which the data entry is uploaded to a database or a cloud network.

If the answer from the decision 310 is yes, then the method 300 continues to a step 320, in which the chosen preset responses are entered. The method 300 thereafter proceeds to another decision step 325 to determine if the user wishes to edit the chosen preset response that is entered. If the answer from the decision step 325 is no, then the method 300 finishes at step 330. If the answer from the decision step 325 is yes, then the method proceeds to the step 315 in which the user edits the preset response that was entered character by character (or via an autocomplete feature).

There are several ways the predefined data entries can be stored on the clinician programmer. In some embodiments, the storage capacity of the clinician programmer is partitioned, and one of the partitions is used for storing preset responses. New predefined responses can be added to this partition, and the new responses on multiple clinician programmers can be synced through use of a remote database. The process of uploading the predefined data entries to the remote database is started with the user entering new predefined data entries. Next, the permission actions sequence is carried out. The process of downloading the predefined date entries is similar, with the user requesting predefined date entries and receiving them based on permissions. Multiple users can therefore draw on each other's date entries.

Figure 6A:
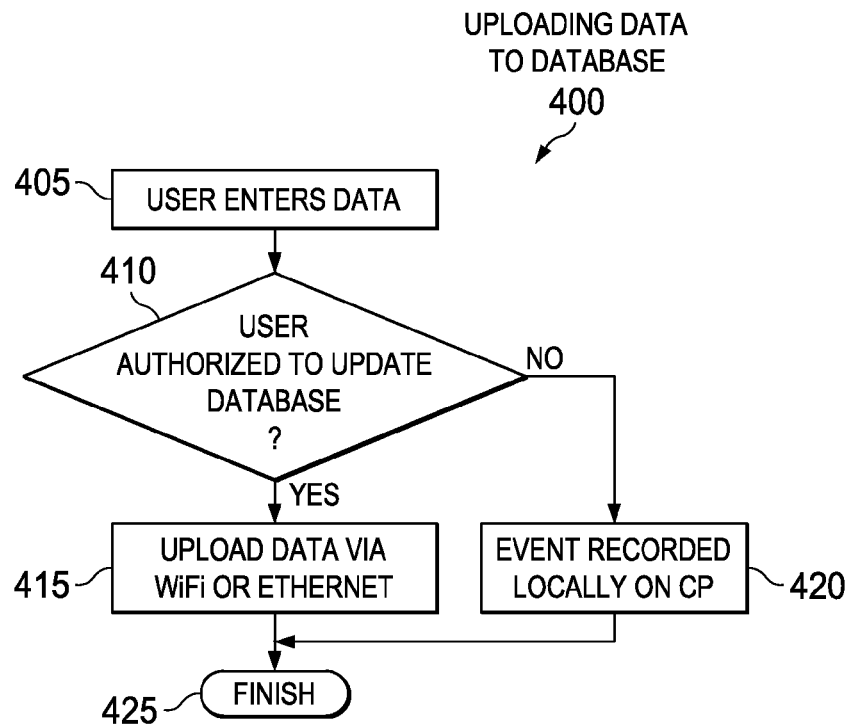
Figure 6B:
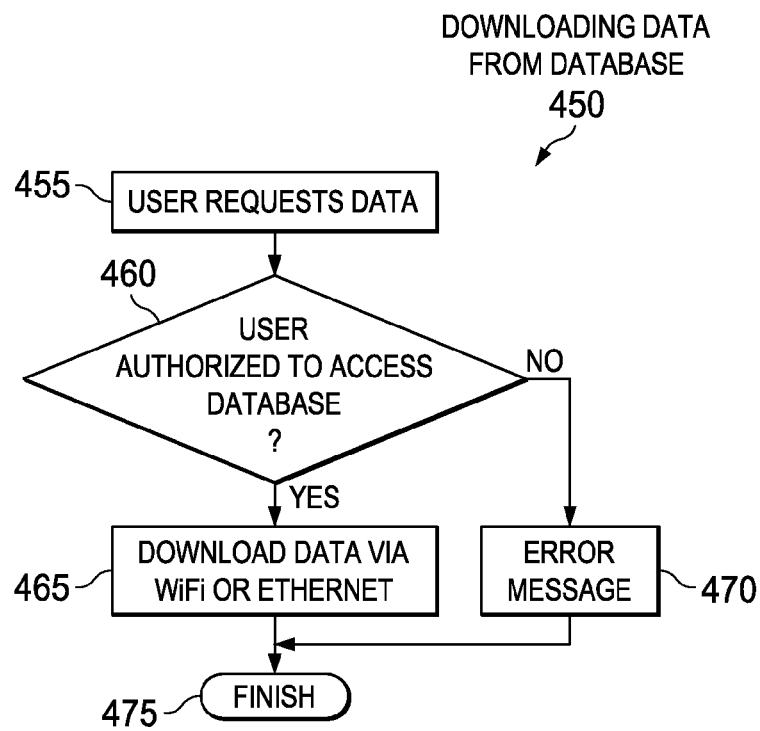

The process of storing, uploading, and downloading the predefined data entries is at least partially reflected in FIGS. 6A-6B, which are flowcharts of simplified example methods 400 and 450 that illustrate communication between a healthcare professional (i.e., the user) using the clinician programmer and a remote database. Referring first to FIG. 6A, the method 400 pertains to the uploading of data from the clinician programmer to the database. The method 400 includes step 405 in which the user enters data. Next, a decision step 410 determines whether the user is authorized to update the database. If the answer is yes, then the database is updated in step 415 by uploading data via a wireless or wired network, such as Wi-Fi or Ethernet. If the user is not authorized to update the database, the method 400 proceeds to step 420, where the attempted update event is recorded locally on the clinician programmer. The method 400 thereafter finishes in step 425.

Referring first to FIG. 6B, the method 450 pertains to the downloading of data from the database to the clinician programmer. The method 400 includes step 455 in which the user requests data. Next, a decision step 460 determines whether the user is authorized to access the database. If the answer is yes, then the database is accessed in step 465 and the requested data is downloaded via a wireless or wired network, such as WiFi or Ethernet. If the user is not authorized to access the database, the method 450 proceeds to step 470, where an error message is displayed on the clinician programmer. The method 450 thereafter finishes in step 475.

Figure 7:
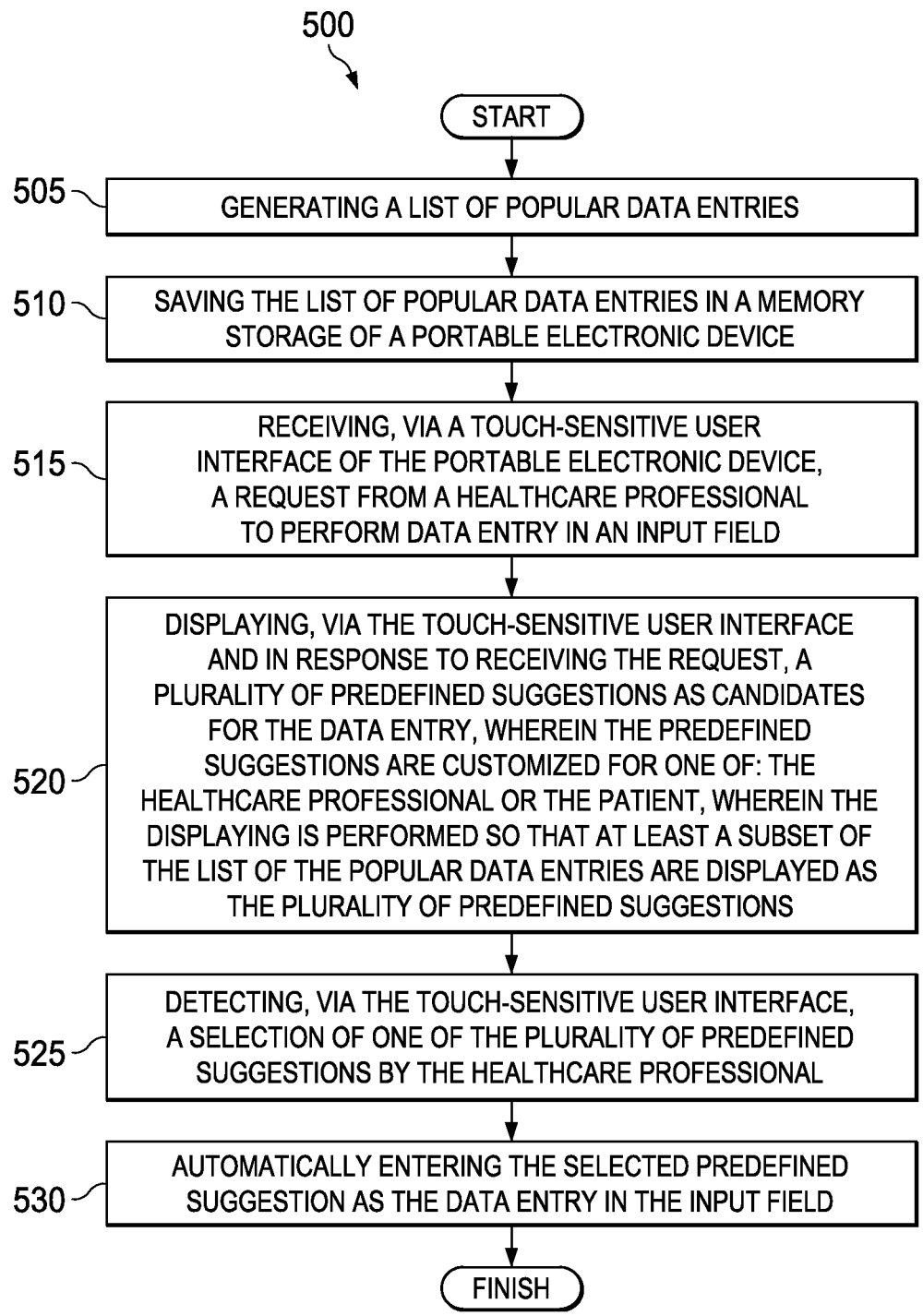

FIG. 7 is a simplified flowchart of a method 500 of entering data in a portable electronic device according to the various aspects of the present disclosure. In some embodiments, the portable electronic device is a clinician programmer. It is understood that additional process steps may be performed before, during, or after the steps 505-530. Furthermore, the steps 505-530 need not be performed in the numerical order shown in FIG. 7. It is also understood that one or more steps 505-530 of the method 300 may be performed at least in part via one or more electronic processors.

The method 500 includes a step 505 of generating a list of popular data entries. In some embodiments, the popular data entries are at least in part predefined based on a surgical procedure performed on the patient. In some embodiments, the step 505 includes a step of defining the popular data entries in response to feedback from the healthcare professional. In other embodiments, the method 500 may further include a step of analyzing popular data entries stored on other portable electronic devices. In those embodiments, the step 505 of generating the list of popular data entries includes selecting at least a subset of popular data entries stored on other portable electronic devices.

The method 500 includes a step 510 of saving the list of popular data entries in a memory storage of the portable electronic device.

The method 500 includes a step 515 of receiving, via a touch-sensitive user interface of the portable electronic device, a request from a healthcare professional to perform data entry in an input field.

The method 500 includes a step 520 of displaying, via the touch-sensitive user interface and in response to the receiving the request, a plurality of predefined suggestions as candidates for the data entry. The predefined suggestions are customized for one of: the healthcare professional or the patient. In some embodiments, the step 520 of displaying is performed so that at least a subset of the list of the popular data entries is displayed as the plurality of predefined suggestions.

The method 500 includes a step 525 of detecting, via the touch-sensitive user interface, a selection of one of the plurality of predefined suggestions by the healthcare professional.

The method 500 includes a step 530 of automatically entering the selected predefined suggestion as the data entry in the input field.

In some embodiments, at least some of the predefined suggestions include blank spaces reserved for patient-specific information.

In some embodiments, the data entry is directed to a patient file, and the method 500 may further include the following steps: a step of analyzing an existing data content in the patient file; and a step of recommending the predefined suggestions based on the analyzed content.

In some embodiments, the method 500 may further comprise a step of assigning a respective rank to each of the plurality of predefined suggestions according to one or more predetermined criteria. In these embodiments, the step 520 of displaying the predefined suggestions includes display the plurality of predefined suggestions according to their respective ranks. In some embodiments, the predetermined criteria include frequency of past use of each of the predefined suggestions. In some embodiments, the predetermined criteria include proximity of plurality of medical devices to the portable electronic device, wherein the data entry is directed toward the medical devices.

Figure 8:
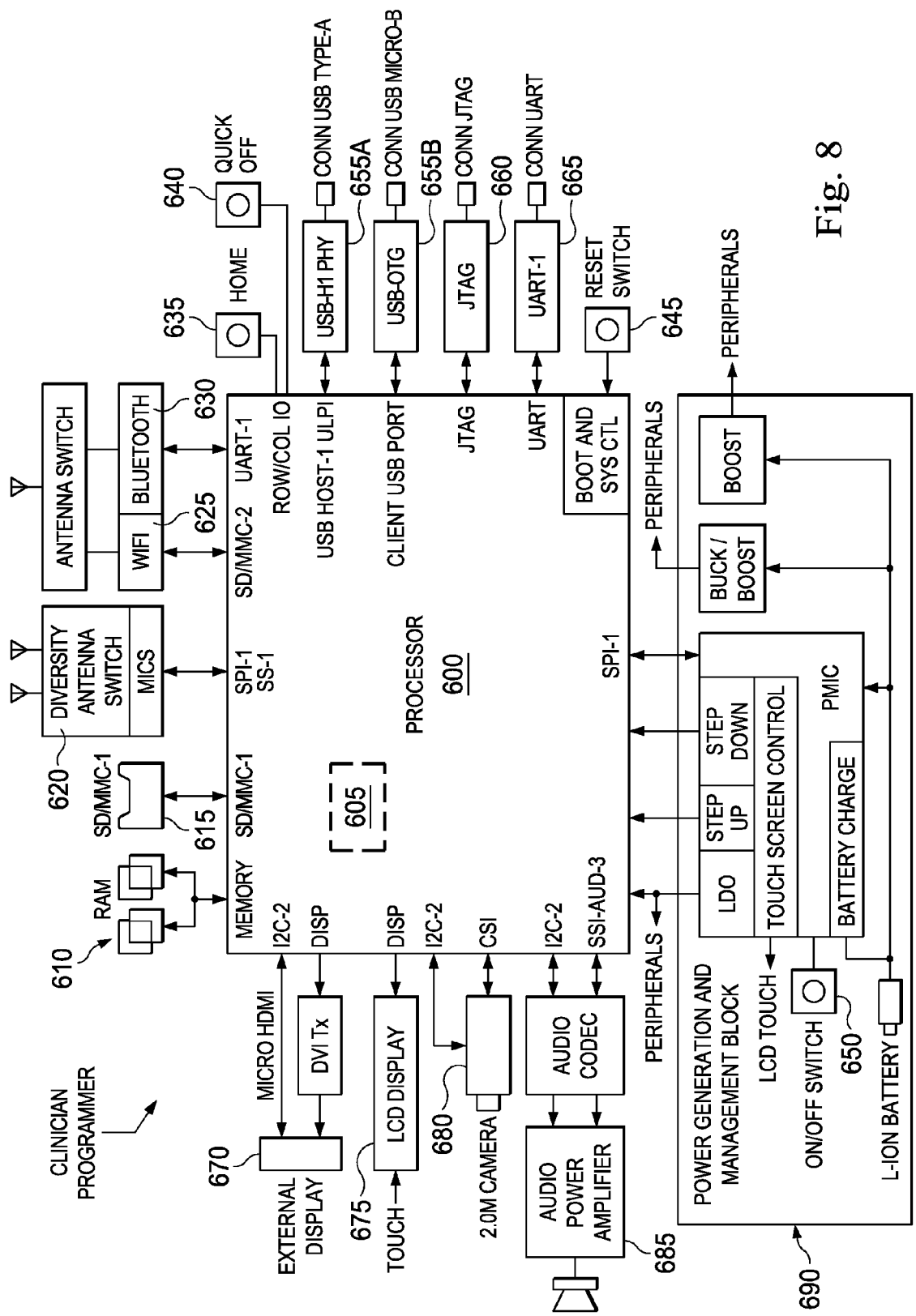
FIG. 8 is a simplified block diagram of an electronic programmer according to various aspects of the present disclosure.

FIG. 8 shows a block diagram of one embodiment of the electronic programmer (CP) discussed herein. For example, the electronic programmer may be a clinician programmer (CP) configured to perform the data entry discussed above. It is understood, however, that alternative embodiments of the electronic programmer may be used to perform these representations as well.

The CP includes a printed circuit board ("PCB") that is populated with a plurality of electrical and electronic components that provide power, operational control, and protection to the CP. With reference to FIG. 8, the CP includes a processor 600. The processor 600 controls the CP. In one construction, the processor 600 is an applications processor model i.MX515 available from Free scale Semiconductor ®. More specifically, the i.MX515 applications processor has internal instruction and data caches, multimedia capabilities, external memory interfacing, and interfacing flexibility. Further information regarding the i.MX515 applications processor can be found in, for example, the "IMX51CEC, Rev. 4" data sheet dated August 2010 and published by Free scale Semiconductor ® at www.freescale.com. The content of the data sheet is incorporated herein by reference. Of course, other processing units, such as other microprocessors, microcontrollers, digital signal processors, etc., can be used in place of the processor 600.

The CP includes memory, which can be internal to the processor 600 (e.g., memory 605), external to the processor 600 (e.g., memory 610), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 600 executes software that is capable of being stored in the RAM (e.g., during execution), the ROM (e.g., on a generally permanent basis), or another non-transitory computer readable medium such as another memory or a disc. The CP also includes input/output ("I/O") systems that include routines for transferring information between components within the processor 600 and other components of the CP or external to the CP.

Software included in the implementation of the CP is stored in the memory 605 of the processor 600, RAM 610, ROM 615, or external to the CP. The software includes, for example, firmware, one or more applications, program data, one or more program modules, and other executable instructions. The processor 600 is configured to retrieve from memory and execute, among other things, instructions related to the control processes and methods described below for the CP.

One memory shown in FIG. 8 is memory 610, which may be a double data rate (DDR2) synchronous dynamic random access memory (SDRAM) for storing data relating to and captured during the operation of the CP. In addition, a secure digital (SD) multimedia card (MMC) may be coupled to the CP for transferring data from the CP to the memory card via slot 615. Of course, other types of data storage devices may be used in place of the data storage devices shown in FIG. 8.

The CP includes multiple bi-directional radio communication capabilities. Specific wireless portions included with the CP are a Medical Implant Communication Service (MICS) bi-directional radio communication portion 620, a Wi-Fi bi-directional radio communication portion 625, and a Bluetooth bi-directional radio communication portion 630. The MICS portion 620 includes a MICS communication interface, an antenna switch, and a related antenna, all of which allows wireless communication using the MICS specification. The Wi-Fi portion 625 and Bluetooth portion 630 include a Wi-Fi communication interface, a Bluetooth communication interface, an antenna switch, and a related antenna all of which allows wireless communication following the Wi-Fi Alliance standard and Bluetooth Special Interest Group standard. Of course, other wireless local area network (WLAN) standards and wireless personal area networks (WPAN) standards can be used with the CP.

The CP includes three hard buttons: a "home" button 635 for returning the CP to a home screen for the device, a "quick off" button 640 for quickly deactivating stimulation IPG, and a "reset" button 645 for rebooting the CP. The CP also includes an "ON/OFF" switch 650, which is part of the power generation and management block (discussed below).

The CP includes multiple communication portions for wired communication. Exemplary circuitry and ports for receiving a wired connector include a portion and related port for supporting universal serial bus (USB) connectivity 655, including a Type A port and a Micro-B port; a portion and related port for supporting Joint Test Action Group (JTAG) connectivity 660, and a portion and related port for supporting universal asynchronous receiver/transmitter (UART) connectivity 665. Of course, other wired communication standards and connectivity can be used with or in place of the types shown in FIG. 8.

Another device connectable to the CP, and therefore supported by the CP, is an external display. The connection to the external display can be made via a micro High-Definition Multimedia Interface (HDMI) 670, which provides a compact audio/video interface for transmitting uncompressed digital data to the external display. The use of the HDMI connection 670 allows the CP to transmit video (and audio) communication to an external display. This may be beneficial in situations where others (e.g., the surgeon) may want to view the information being viewed by the healthcare professional. The surgeon typically has no visual access to the CP in the operating room unless an external screen is provided. The HDMI connection 670 allows the surgeon to view information from the CP, thereby allowing greater communication between the clinician and the surgeon. For a specific example, the HDMI connection 670 can broadcast a high definition television signal that allows the surgeon to view the same information that is shown on the LCD (discussed below) of the CP.

The CP includes a touch screen I/O device 675 for providing a user interface with the clinician. The touch screen display 675 can be a liquid crystal display (LCD) having a resistive, capacitive, or similar touch-screen technology. It is envisioned that multitouch capabilities can be used with the touch screen display 675 depending on the type of technology used.

The CP includes a camera 680 allowing the device to take pictures or video. The resulting image files can be used to document a procedure or an aspect of the procedure. Other devices can be coupled to the CP to provide further information, such as scanners or RFID detection. Similarly, the CP includes an audio portion 685 having an audio codec circuit, audio power amplifier, and related speaker for providing audio communication to the user, such as the clinician or the surgeon.

The CP further includes a power generation and management block 690. The power block 690 has a power source (e.g., a lithium-ion battery) and a power supply for providing multiple power voltages to the processor, LCD touch screen, and peripherals.

In one embodiment, the CP is a handheld computing tablet with touch screen capabilities. The tablet is a portable personal computer with a touch screen, which is typically the primary input device. However, an external keyboard or mouse can be attached to the CP. The tablet allows for mobile functionality not associated with even typical laptop personal computers. The hardware may include a Graphical Processing Unit (GPU) in order to speed up the user experience. An Ethernet port (not shown in FIG. 8) may also be included for data transfer.

It is understood that a patient programmer may be implemented in a similar manner as the clinician programmer shown in FIG. 8.

Figure 9:
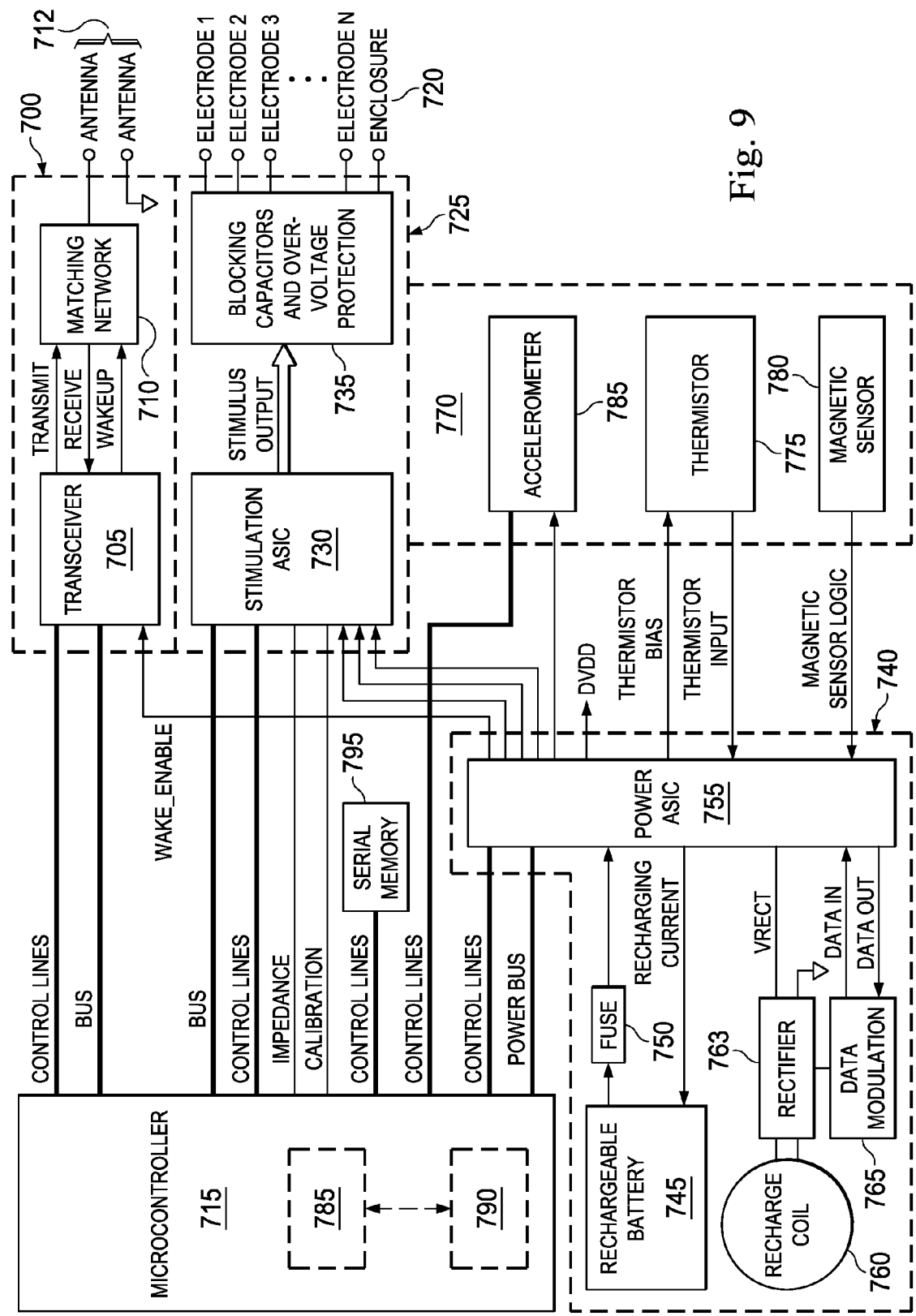
FIG. 9 is a simplified block diagram of an implantable medical device according to various aspects of the present disclosure.

FIG. 9 shows a block diagram of one embodiment of an implantable medical device. In the embodiment shown in FIG. 9, the implantable medical device includes an implantable pulse generator (IPG). The IPG includes a printed circuit board ("PCB") that is populated with a plurality of electrical and electronic components that provide power, operational control, and protection to the IPG. With reference to FIG. 9, the IPG includes a communication portion 700 having a transceiver 705, a matching network 710, and antenna 712. The communication portion 700 receives power from a power ASIC (discussed below), and communicates information to/from the microcontroller 715 and a device (e.g., the CP) external to the IPG. For example, the IPG can provide bi-direction radio communication capabilities, including Medical Implant Communication Service (MICS) bi-direction radio communication following the MICS specification.

The IPG provides stimuli to electrodes of an implanted medical electrical lead (not illustrated herein). As shown in FIG. 9, N electrodes are connected to the IPG. In addition, the enclosure or housing 720 of the IPG can act as an electrode. The stimuli are provided by a stimulation portion 225 in response to commands from the microcontroller 215. The stimulation portion 725 includes a stimulation application specific integrated circuit (ASIC) 730 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, FLASH, etc. The stimulation ASIC 730 can include a processor, memory, and firmware for storing preset pulses and protocols that can be selected via the microcontroller 715. The providing of the pulses to the electrodes is controlled through the use of a waveform generator and amplitude multiplier of the stimulation ASIC 730, and the blocking capacitors and overvoltage protection circuitry 735 of the stimulation portion 725, as is known in the art. The stimulation portion 725 of the IPG receives power from the power ASIC (discussed below). The stimulation ASIC 730 also provides signals to the microcontroller 715. More specifically, the stimulation ASIC 730 can provide impedance values for the channels associated with the electrodes, and also communicate calibration information with the microcontroller 715 during calibration of the IPG.

The IPG also includes a power supply portion 740. The power supply portion includes a rechargeable battery 745, fuse 750, power ASIC 755, recharge coil 760, rectifier 763 and data modulation circuit 765. The rechargeable battery 745 provides a power source for the power supply portion 740. The recharge coil 760 receives a wireless signal from the PPC. The wireless signal includes an energy that is converted and conditioned to a power signal by the rectifier 763. The power signal is provided to the rechargeable battery 745 via the power ASIC 755. The power ASIC 755 manages the power for the IPG. The power ASIC 755 provides one or more voltages to the other electrical and electronic circuits of the IPG. The data modulation circuit 765 controls the charging process.

The IPG also includes a magnetic sensor 780. The magnetic sensor 780 provides a "hard" switch upon sensing a magnet for a defined period. The signal from the magnetic sensor 780 can provide an override for the IPG if a fault is occurring with the IPG and is not responding to other controllers.

The IPG is shown in FIG. 9 as having a microcontroller 715. Generally speaking, the microcontroller 715 is a controller for controlling the IPG. The microcontroller 715 includes a suitable programmable portion 785 (e.g., a microprocessor or a digital signal processor), a memory 790, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at www.ti.com; the content of the data sheet being incorporated herein by reference.

The IPG includes memory, which can be internal to the control device (such as memory 790), external to the control device (such as serial memory 795), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 785 executes software that is capable of being stored in the RAM (e.g., during execution), the ROM (e.g., on a generally permanent basis), or another non-transitory computer readable medium such as another memory or a disc.

Software included in the implementation of the IPG is stored in the memory 790. The software includes, for example, firmware, one or more applications, program data, one or more program modules, and other executable instructions. The programmable portion 785 is configured to retrieve from memory and execute, among other things, instructions related to the control processes and methods described below for the IPG. For example, the programmable portion 285 is configured to execute instructions retrieved from the memory 790 for sweeping the electrodes in response to a signal from the CP.

Figure 10:
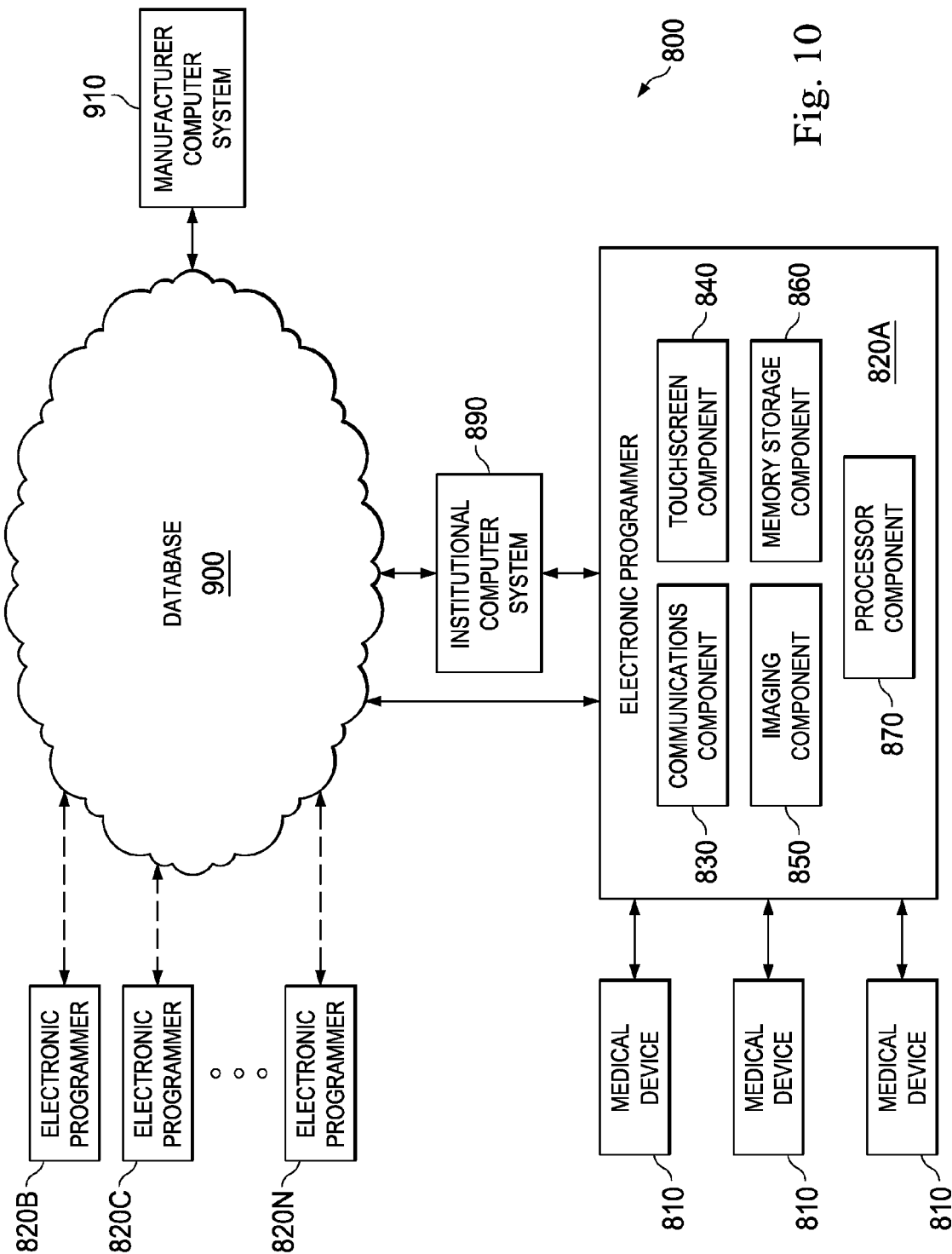
FIG. 10 is a simplified block diagram of a medical system/infrastructure according to various aspects of the present disclosure.

Referring now to FIG. 10, a simplified block diagram of a medical infrastructure 800 (which may also be considered a medical system) is illustrated according to various aspects of the present disclosure. The medical infrastructure 800 includes a plurality of medical devices 810. These medical devices 810 may each be a programmable medical device (or parts thereof) that can deliver a medical therapy to a patient. In some embodiments, the medical devices 810 may include a device of the neurostimulator system discussed above with reference to FIG. 1. For example, the medical devices 810 may be a pulse generator (e.g., the IPG discussed above with reference to FIG. 9), an implantable lead, a charger, or portions thereof. It is understood that each of the medical devices 810 may be a different type of medical device. In other words, the medical devices 810 need not be the same type of medical device. The medical device 810 includes a memory storage component configured to store data. In some embodiments, the memory storage component is partitioned into multiple partitions that are each configured to store a different type of data.

The medical infrastructure 800 also includes a plurality of electronic programmers 820. For sake of illustration, one of these electronic programmers 820A is illustrated in more detail and discussed in detail below. Nevertheless, it is understood that each of the electronic programmers 820 may be implemented similar to the electronic programmer 820A.

In some embodiments, the electronic programmer 820A may be a clinician programmer, for example the clinician programmer discussed above with reference to FIG. 8. In other embodiments, the electronic programmer 820A may be a patient programmer or another similar programmer. In further embodiments, it is understood that the electronic programmer may be a tablet computer. In any case, the electronic programmer 820A is configured to program the stimulation parameters of the medical devices 810 so that a desired medical therapy can be delivered to a patient.

The electronic programmer 820A contains a communications component 830 that is configured to conduct electronic communications with external devices. For example, the communications device 830 may include a transceiver. The transceiver contains various electronic circuitry components configured to conduct telecommunications with one or more external devices. The electronic circuitry components allow the transceiver to conduct telecommunications in one or more of the wired or wireless telecommunications protocols, including communications protocols such as IEEE 802.11 (Wi-Fi), IEEE 802.15 (Bluetooth), GSM, CDMA, LTE, WIMAX, DLNA, HDMI, Medical Implant Communication Service (MICS), etc. In some embodiments, the transceiver includes antennas, filters, switches, various kinds of amplifiers such as low-noise amplifiers or power amplifiers, digital-to-analog (DAC) converters, analog-to-digital (ADC) converters, mixers, multiplexers and demultiplexers, oscillators, and/or phase-locked loops (PLLs). Some of these electronic circuitry components may be integrated into a single discrete device or an integrated circuit (IC) chip.

The electronic programmer 820A contains a touchscreen component 840. The touchscreen component 840 may display a touch-sensitive graphical user interface that is responsive to gesture-based user interactions. The touch-sensitive graphical user interface may detect a touch or a movement of a user's finger(s) on the touchscreen and interpret these user actions accordingly to perform appropriate tasks. The graphical user interface may also utilize a virtual keyboard to receive user input. In some embodiments, the touch-sensitive screen may be a capacitive touchscreen. In other embodiments, the touch-sensitive screen may be a resistive touchscreen.

It is understood that the electronic programmer 820A may optionally include additional user input/output components that work in conjunction with the touchscreen component 840 to carry out communications with a user. For example, these additional user input/output components may include physical and/or virtual buttons (such as power and volume buttons) on or off the touch-sensitive screen, physical and/or virtual keyboards, mouse, track balls, speakers, microphones, light-sensors, light-emitting diodes (LEDs), communications ports (such as USB or HDMI ports), joy-sticks, etc.

The electronic programmer 820A contains an imaging component 850. The imaging component 850 is configured to capture an image of a target device via a scan. For example, the imaging component 850 may be a camera in some embodiments. The camera may be integrated into the electronic programmer 820A. The camera can be used to take a picture of a medical device, or scan a visual code of the medical device, for example its barcode or Quick Response (QR) code.

The electronic programmer contains a memory storage component 860. The memory storage component 860 may include system memory, (e.g., RAM), static storage 608 (e.g., ROM), or a disk drive (e.g., magnetic or optical), or any other suitable types of computer readable storage media. For example, some common types of computer readable media may include floppy disk, flexible disk, hard disk, magnetic tape, any other magnetic medium, CD-ROM, any other optical medium, RAM, PROM, EPROM, FLASH-EPROM, any other memory chip or cartridge, or any other medium from which a computer is adapted to read. The computer readable medium may include, but is not limited to, non-volatile media and volatile media. The computer readable medium is tangible, concrete, and non-transitory. Logic (for example in the form of computer software code or computer instructions) may be encoded in such computer readable medium. In some embodiments, the memory storage component 860 (or a portion thereof) may be configured as a local database capable of storing electronic records of medical devices and/or their associated patients.

The electronic programmer contains a processor component 870. The processor component 870 may include a central processing unit (CPU), a graphics processing unit (GPU) a micro-controller, a digital signal processor (DSP), or another suitable electronic processor capable of handling and executing instructions. In various embodiments, the processor component 870 may be implemented using various digital circuit blocks (including logic gates such as AND, OR, NAND, NOR, XOR gates, etc.) along with certain software code. In some embodiments, the processor component 870 may execute one or more sequences computer instructions contained in the memory storage component 860 to perform certain tasks.

It is understood that hard-wired circuitry may be used in place of (or in combination with) software instructions to implement various aspects of the present disclosure. Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

It is also understood that the electronic programmer 820A is not necessarily limited to the components 830-870 discussed above, but it may further include additional components that are used to carry out the programming tasks. These additional components are not discussed herein for reasons of simplicity. It is also understood that the medical infrastructure 800 may include a plurality of electronic programmers similar to the electronic programmer 820A discussed herein, but they are not illustrated in FIG. 10 for reasons of simplicity.

The medical infrastructure 800 also includes an institutional computer system 890. The institutional computer system 890 is coupled to the electronic programmer 820A. In some embodiments, the institutional computer system 890 is a computer system of a healthcare institution, for example a hospital. The institutional computer system 890 may include one or more computer servers and/or client terminals that may each include the necessary computer hardware and software for conducting electronic communications and performing programmed tasks. In various embodiments, the institutional computer system 890 may include communications devices (e.g., transceivers), user input/output devices, memory storage devices, and computer processor devices that may share similar properties with the various components 830-870 of the electronic programmer 820A discussed above. For example, the institutional computer system 890 may include computer servers that are capable of electronically communicating with the electronic programmer 820A through the MICS protocol or another suitable networking protocol.

The medical infrastructure 800 includes a database 900. In various embodiments, the database 900 is a remote database—that is, located remotely to the institutional computer system 890 and/or the electronic programmer 820A. The database 900 is electronically or communicatively (for example through the Internet) coupled to the institutional computer system 890 and/or the electronic programmer. In some embodiments, the database 900, the institutional computer system 890, and the electronic programmer 820A are parts of a cloud-based architecture. In that regard, the database 900 may include cloud-based resources such as mass storage computer servers with adequate memory resources to handle requests from a variety of clients. The institutional computer system 890 and the electronic programmer 820A (or their respective users) may both be considered clients of the database 900. In certain embodiments, the functionality between the cloud-based resources and its clients may be divided up in any appropriate manner. For example, the electronic programmer 820A may perform basic input/output interactions with a user, but a majority of the processing and caching may be performed by the cloud-based resources in the database 900. However, other divisions of responsibility are also possible in various embodiments.

According to the various aspects of the present disclosure, the predefined data entries may be uploaded from the electronic programmer 820A to the database 900. The predefined data entries saved in the database 900 may thereafter be downloaded by any of the other electronic programmers 820B-820N communicatively coupled to it, assuming the user of these programmers has the right login permissions. For example, predefined data entries may be generated by the electronic programmer 820A and uploaded to the database 900. These predefined data entries can then be downloaded by the electronic programmer 820B.

The database 900 may also include a manufacturer's database in some embodiments. It may be configured to manage an electronic medical device inventory, monitor manufacturing of medical devices, control shipping of medical devices, and communicate with existing or potential buyers (such as a healthcare institution). For example, communication with the buyer may include buying and usage history of medical devices and creation of purchase orders. A message can be automatically generated when a client (for example a hospital) is projected to run out of equipment, based on the medical device usage trend analysis done by the database. According to various aspects of the present disclosure, the database 900 is able to provide these functionalities at least in part via communication with the electronic programmer 820A and in response to the data sent by the electronic programmer 820A. These functionalities of the database 900 and its communications with the electronic programmer 820A will be discussed in greater detail later.

The medical infrastructure 800 further includes a manufacturer computer system 910. The manufacturer computer system 910 is also electronically or communicatively (for example through the Internet) coupled to the database 900. Hence, the manufacturer computer system 910 may also be considered a part of the cloud architecture. The computer system 910 is a computer system of medical device manufacturer, for example a manufacturer of the medical devices 810 and/or the electronic programmer 820A.

In various embodiments, the manufacturer computer system 910 may include one or more computer servers and/or client terminals that each includes the necessary computer hardware and software for conducting electronic communications and performing programmed tasks. In various embodiments, the manufacturer computer system 910 may include communications devices (e.g., transceivers), user input/output devices, memory storage devices, and computer processor devices that may share similar properties with the various components 830-870 of the electronic programmer 820A discussed above. Since both the manufacturer computer system 910 and the electronic programmer 820A are coupled to the database 900, the manufacturer computer system 910 and the electronic programmer 820A can conduct electronic communication with each other.

Figure 11A:
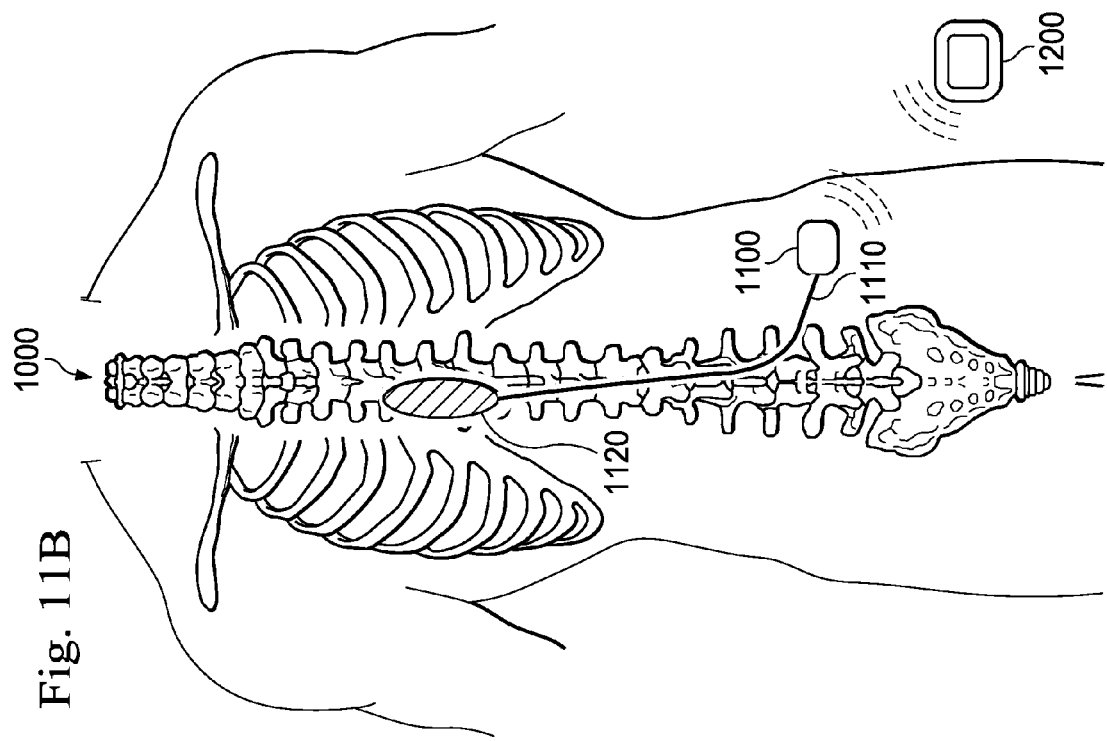
FIGS. 11A and 11B are side and posterior views of a human spine, respectively.
Figure 11B:
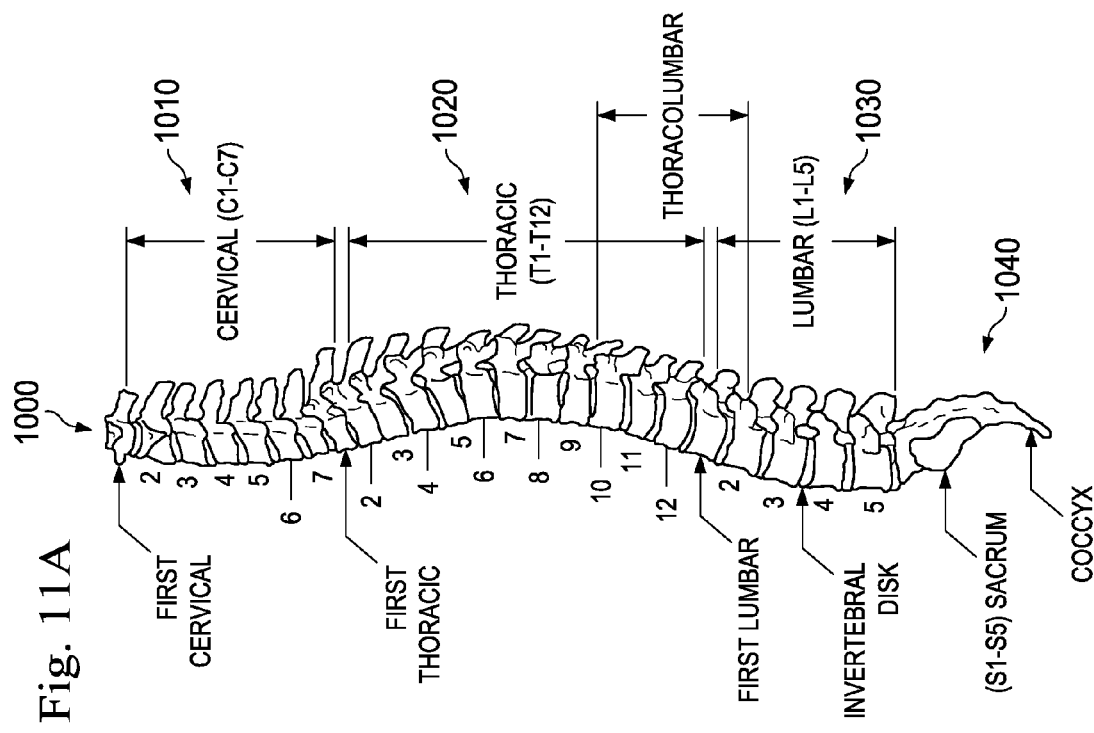

FIG. 11A is a side view of a spine 1000, and FIG. 11B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 11B, an IPG device 1100 is implanted inside the body. The IPG device 1100 may include a neurostimulator device. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200, the implementation of which may be similar to the clinician programmer shown in FIG. 8.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A portable electronic device, comprising:
    a touch-sensitive user interface configured to receive an input from a user and display an output to the user;
    a memory storage configured to store programming instructions;
    one or more electronic processors configured to execute the programming instructions to perform programming of a pulse generator to deliver an electrical stimulation therapy for a patient, wherein the programming includes the following steps:
        receiving a request from a healthcare professional to perform data entry in a text input field in which textual information can be entered via a virtual keyboard, wherein the receiving the request comprises detecting a click of the text input field via the touch-sensitive user interface;
        displaying, on a region of the touch-sensitive user interface, a plurality of predefined suggestions as candidates for the data entry, wherein the predefined suggestions are customized for one of: the healthcare professional or the patient, and wherein the plurality of predefined suggestions are previously hidden, and an appearance of the predefined suggestions is triggered in response to the detecting the click of the text input field and without using the virtual keyboard;
        detecting a selection of one of the plurality of predefined suggestions by detecting a touch of the region of the touch-sensitive user interface made by the healthcare professional;
        automatically entering the selected predefined suggestion as the data entry in the text input field without the use of the virtual keyboard, wherein the predefined suggestions are editable after being entered in the text input field; and
        programming, in response to stimulation parameters received from the user, the pulse generator to deliver the electrical stimulation therapy to treat the patient, wherein the stimulation parameters include one or more of: stimulation pulse amplitude, stimulation pulse frequency, stimulation pulse width, electrode polarity, and electrode combination.

2. The portable electronic device of claim 1, wherein the steps further comprise:
generating a list of popular data entries;
saving the list of popular data entries in the memory storage; and
selecting at least a subset of the list of popular data entries to be displayed as the plurality of predefined suggestions.

3. The portable electronic device of claim 2, wherein the generating the list of popular data entries comprises defining the popular data entries in response to feedback from the healthcare professional.

4. The portable electronic device of claim 2, wherein the steps further comprise: analyzing popular data entries stored on other portable electronic devices, wherein the generating the list of popular data entries comprises selecting at least a subset of popular data entries stored on the other portable electronic devices.

5. The portable electronic device of claim 2, wherein the popular data entries are at least in part predefined based on a surgical procedure performed on the patient.

6. The portable electronic device of claim 1, wherein at least some of the predefined suggestions include blank spaces reserved for patient-specific information.

7. The portable electronic device of claim 1, wherein the data entry is directed to a patient file, and wherein the steps further comprise:
analyzing an existing data content in the patient file; and
recommending the predefined suggestions based on the analyzed content.

8. The portable electronic device of claim 1., wherein the displaying comprises:
assigning a respective rank to each of the plurality of predefined suggestions according to one or more predetermined criteria; and
displaying the plurality of predefined suggestions according to their respective ranks.

9. The portable electronic device of claim 8, wherein the predetermined criteria include frequency of past use of each of the predefined suggestions.

10. The portable electronic device of claim 8, wherein the data entry is directed to a patient file, and wherein the predetermined criteria include correlation between each of the predefined suggestions and an existing data content in the patient file.

11. The portable electronic device of claim 8, wherein the predetermined criteria include proximity of plurality of medical devices to the portable electronic device, and wherein the data entry is directed toward the medical devices.

12. The portable electronic device of claim 1, wherein the portable electronic device includes a clinician programmer.

13. A medical system, comprising:
a portable electronic device having a touch-sensitive user interface through which data entry is performed with respect to an electrical stimulation therapy, wherein the portable electronic device includes a non-transitory computer readable medium comprising executable instructions that when executed by a processor, causes the processor to perform the steps of:
receiving a request from a healthcare professional to perform data entry in a text input field in which textual information can be entered via a virtual keyboard, wherein the receiving the request comprises detecting a click of the text input field via the touch-sensitive user interface;
displaying, on a region of the touch-sensitive user interface, a plurality of predefined suggestions as candidates for the data entry, wherein the predefined suggestions are customized for one of: the healthcare professional or a patient, and wherein the plurality of predefined suggestions are previously hidden, and an appearance of the predefined suggestions is triggered in response to the detecting the click of the text input field and without using the virtual keyboard, wherein the displaying further comprises:
assigning a respective rank to each of the plurality of predefined suggestions according to a one or more predetermined criteria including a frequency of past use of each of the predefined suggestions; and
displaying the plurality of predefined suggestions according to their respective ranks;
detecting, via the touch-sensitive user interface, a selection of one of the plurality of predefined suggestions by detecting a touch of the region of the touch-sensitive user interface made by the healthcare professional;
automatically entering the selected predefined suggestion as the data entry in the text input field without the use of the virtual keyboard; and
electronically transmitting programming instructions to a pulse generator, the programming instructions specifying stimulation parameters that include one or more of: stimulation pulse amplitude, stimulation pulse frequency, stimulation pulse width, electrode polarity, and electrode combination;
a pulse generator configured to:
receive the programming instructions; and
generate electrical pulses as a part of the electrical stimulation therapy based on the received programming instructions.

14. The medical system of claim 13, wherein the steps further comprise:
generating a list of popular data entries;
saving the list of popular data entries in an electronic memory storage; and
selecting at least a subset of the list of popular data entries to be displayed as the plurality of predefined suggestions.

15. The medical system of claim 14, wherein the generating the list of popular data entries comprises defining the popular data entries in response to feedback from the healthcare professional.

16. The medical system of claim 14, wherein the steps further comprise: analyzing popular data entries stored on other portable electronic devices, wherein the generating the list of popular data entries comprises selecting at least a subset of popular data entries stored on the other portable electronic devices.

17. The medical system of claim 14, therein the popular data entries are at east in part predefined based on a surgical procedure performed on the patient.

18. The medical system of claim 13, wherein at least some of the predefined suggestions include blank spaces reserved for patient-specific information.

19. The medical system of claim 13, wherein the data entry is directed to a patient file, and wherein the steps further comprise:

analyzing an existing data content in the patient file; and
recommending the predefined suggestions based on the analyzed content.

20. The medical system of claim 13 wherein the data entry is directed to a patient file, and wherein the predetermined criteria include correlation between each of the predefined suggestions and an existing data content in the patient file.

21. The medical system of claim 13, wherein the predetermined criteria include proximity of plurality of medical devices to the portable electronic device, and wherein the data entry is directed toward the medical devices.

22. The medical system of claim 13, wherein:
the pulse generator includes an implanted pulse generator (IPG); and
the portable electronic device includes a clinician programmer.

23. The medical system of claim 13, wherein the predefined suggestions are editable after being entered in the text input field.

24. A method of entering data in a portable electronic device, the method comprising:
receiving a request from a healthcare professional to perform data entry in a text input field in which textual information can be entered via a virtual keyboard, wherein the receiving the request comprises detecting a click of the text input field via a touch-sensitive user interface, and wherein the data entry is directed to a patient file;
displaying, on a region of the touch-sensitive user interface, a plurality of predefined suggestions as candidates for the data entry, wherein the predefined suggestions are customized for one of: the healthcare professional or the patient, and wherein the plurality of predefined suggestions are previously hidden, and an appearance of the predefined suggestions is triggered in response to the detecting the click of the text input field and without using the virtual keyboard;
analyzing an existing data content in the patient file;
recommending the predefined suggestions based on the analyzed content;
detecting a selection of one of the plurality of predefined suggestions by detecting a touch of the region of the touch-sensitive user interface made by the healthcare professional;
automatically entering the selected predefined suggestion as the data entry in the text input field without the use of the virtual keyboard; and
programming a pulse generator to generate electrical stimulation pulses based at least in part on the data entry, wherein the programming the pulse generator includes sending, to the pulse generator, stimulation parameters that include one or more of: stimulation pulse amplitude, stimulation pulse frequency, stimulation pulse width, electrode polarity, and electrode combination.

25. The method of claim 24, further comprising:
generating a list of popular data entries;
saving the list of popular data entries in a memory storage of the portable electronic device: and
selecting at least a subset of the list of popular data entries to be displayed as the plurality of predefined suggestions.

26. The method of claim 25, wherein the generating the list of popular data entries comprises defining the popular data entries in response to feedback from the healthcare professional.

27. The method of claim 25, further comprising: analyzing popular data entries stored on other portable electronic devices, wherein the generating the list of popular data entries comprises selecting at least a subset of popular data entries stored on the other portable electronic devices.

28. The method of claim 25, wherein the popular data entries are at least in part predefined based on a surgical procedure performed on the patient.

29. The method of claim 24, wherein at least some of the predefined suggestions include blank spaces reserved for patient-specific information.

30. The method of claim 24, wherein the displaying comprises:
assigning a respective rank to each of the plurality of predefined suggestions according to one or more predetermined criteria; and
displaying the plurality of predefined suggestions according to their respective ranks.

31. The method of claim 30, wherein the predetermined criteria include frequency of past use of each of the predefined suggestions.

32. The method of claim 30, wherein the data entry is directed to a patient file, and wherein the predetermined criteria include correlation between each of the predefined suggestions and an existing data content in the patient file.

33. The method of claim 30, wherein the predetermined criteria include proximity of plurality of medical devices to the portable electronic device, and wherein the data entry is directed toward the medical devices.

34. The method of claim 24, wherein the portable electronic device includes a clinician programmer.

35. The method of claim 24, wherein the predefined suggestions are editable after being entered in the text input field.

36. A portable electronic device, comprising:
touchscreen means for receiving an input from a user and displaying an output to the user;
means for receiving a request from a healthcare professional to perform data entry directed to a patient file, the receiving the request comprising detecting, via the touchscreen means, a click in a text input field in which textual information can be entered via a virtual keyboard;
means for displaying, on a region of the touchscreen means, a plurality of predefined suggestions as candidates for the data entry, wherein the predefined suggestions are customized for one of: the healthcare professional or the patient, wherein the plurality of predefined suggestions are previously hidden, and an appearance of the predefined suggestions is triggered in response to the detecting of the click in the text input field and without using the virtual keyboard, and wherein the displaying comprises: assigning a respective rank to each of the plurality of predefined suggestions according to a respective proximity of a plurality of medical devices to the portable electronic device, and displaying the plurality of predefined suggestions according to their respective ranks;
means for detecting a selection of one of the plurality of predefined suggestions by detecting a touch of the region of the touchscreen means made by the healthcare professional;
means for automatically entering the selected predefined suggestion as the data entry in the text input field without the use of the virtual keyboard; and
means for programming a pulse generator according to a plurality of stimulation parameters to deliver an electrical stimulation therapy for a patient the stimulation parameters include one or more of: stimulation pulse amplitude, stimulation pulse frequency, stimulation pulse width, electrode polarity, and electrode combination.

37. The portable electronic device of claim 36, further comprising:
   means for generating a list of popular data entries, wherein the popular data entries are at least in part predefined based on a surgical procedure performed on the patient;
   means for saving the list of popular data entries in an electronic memory storage; and
   means for selecting at least a subset of the list of popular data entries to be displayed as the plurality of predefined suggestions.

38. The portable electronic device of claim 37, wherein the means for generating the list of popular data entries comprises means for defining the popular data entries in response to feedback from the healthcare professional.

39. The portable electronic device of claim 37, further comprising: means for analyzing popular data entries stored on other portable electronic devices, and wherein the means for generating the list of popular data entries comprises means for selecting at least a subset of popular data entries stored on the other portable electronic devices.

40. The portable electronic device of claim 36, further comprising:
   means for analyzing an existing data content in the patient file: and
   means for recommending the predefined suggestions based on the analyzed content.

41. The portable electronic device of claim 36, wherein the predefined suggestions are editable after being entered in the text input field.

* * * * *

UNITED STATES PATENT AND TRADEMARK OFFICE
CERTIFICATE OF CORRECTION

PATENT NO.         : 9,767,255 B2
APPLICATION NO.    : 14/010942
DATED              : September 19, 2017
INVENTOR(S)        : Norbert Kaula et al.

It is certified that error appears in the above-identified patent and that said Letters Patent is hereby corrected as shown below:

In the Claims

Column 19, Line 36 Claim 8 delete "1.," and insert --1.--.

Column 20, Line 60 Claim 17 delete "east" and insert --least--.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*